US010067116B2

(12) United States Patent
Ebi et al.

(10) Patent No.: US 10,067,116 B2
(45) Date of Patent: Sep. 4, 2018

(54) CELL ANALYZER, CELL COLLECTING APPARATUS, AND QUALITY CONTROL METHOD INCLUDING PROCESSING AND ANALYZING QUALITY CONTROL PARTICLES

(71) Applicant: Sysmex Corporation, Kobe-shi, Hyogo (JP)

(72) Inventors: Ryuichiro Ebi, Kobe (JP); Emi Kanemura, Kobe (JP); Kohei Murakami, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 183 days.

(21) Appl. No.: 14/227,742

(22) Filed: Mar. 27, 2014

(65) Prior Publication Data

US 2014/0297200 A1    Oct. 2, 2014

(30) Foreign Application Priority Data

Mar. 29, 2013    (JP) ................................ 2013-073549

(51) Int. Cl.
| | |
|---|---|
| *G01N 33/483* | (2006.01) |
| *G01N 15/14* | (2006.01) |
| *G01N 1/40* | (2006.01) |
| *G01N 35/00* | (2006.01) |

(52) U.S. Cl.
CPC ....... *G01N 33/4833* (2013.01); *G01N 1/4077* (2013.01); *G01N 15/1429* (2013.01); *G01N 15/1434* (2013.01); *G01N 35/00613* (2013.01); *G01N 2001/4088* (2013.01); *G01N 2035/009* (2013.01)

(58) Field of Classification Search
None
See application file for complete search history.

(56) References Cited

U.S. PATENT DOCUMENTS

| | | | | |
|---|---|---|---|---|
| 6,589,792 | B1 * | 7/2003 | Malachowski .... | G01N 15/1404 209/127.4 |
| 8,189,177 | B2 | 5/2012 | Fukuda et al. | |
| 8,415,145 | B2 | 4/2013 | Fukuda et al. | |
| 8,524,153 | B2 | 9/2013 | Mimura et al. | |
| 2005/0112541 | A1 * | 5/2005 | Durack ................ | C12N 5/0612 435/2 |
| 2005/0221399 | A1 | 10/2005 | Nakano et al. | |
| 2008/0108103 | A1 | 5/2008 | Ishisaka et al. | |
| 2009/0091746 | A1 | 4/2009 | Fukuda et al. | |
| 2011/0014646 | A1 | 1/2011 | Fukuda et al. | |
| 2011/0014685 | A1 | 1/2011 | Fukuda et al. | |
| 2011/0076755 | A1 | 3/2011 | Ebi et al. | |
| 2011/0176934 | A1 | 7/2011 | Ebi et al. | |

FOREIGN PATENT DOCUMENTS

| | | |
|---|---|---|
| AU | 2012227165 A1 | 10/2012 |
| CN | 101151517 A | 3/2008 |
| CN | 101983328 A | 3/2011 |
| CN | 102112875 A | 6/2011 |
| CN | 102183451 A | 9/2011 |
| CN | 101038293 B | 11/2011 |
| EP | 0 953 377 A1 | 11/1999 |
| EP | 1 835 291 A2 | 9/2007 |
| EP | 2045595 A2 | 4/2009 |
| EP | 2045595 A3 | 4/2009 |
| EP | 2 261 632 A1 | 12/2010 |
| EP | 2320230 A1 | 5/2011 |
| EP | 2345885 A2 | 7/2011 |
| EP | 2735872 A1 | 5/2014 |
| JP | 06-201569 A | 7/1994 |
| JP | H10-253624 A | 9/1998 |
| JP | 2004-286666 A | 10/2004 |
| JP | 2005-315862 A | 11/2005 |
| JP | 2009-103687 A | 5/2009 |
| WO | WO 01/39870 A2 | 6/2001 |
| WO | WO 2006/103920 A1 | 10/2006 |
| WO | WO 2009/122999 A1 | 10/2009 |

OTHER PUBLICATIONS

Park, "Large liver cell dysplasia: a controversial entity," Journal of hepatology, vol. 45, p. 734-743, 2006.*
Watanabe, "Morphologic studies of the liver cell dysplasia," Cancer, vol. 51, p. 2197-2205, 1983.*
El-Sayed, "DNA ploidy and liver cell dysplasia in liver biopsies from patients with liver cirrhosis," Canadian journal of gastroenterology, vol. 18, p. 87-91, 2004.*
Unknown author, "Diagnosis, Treatment and Management of Gynecological Diseases," Acta Obstetric et Gynaecologica Japonica, vol. 61, No. 4, 2009, pp. N102-N105.
Shah et al., "Morphometric Pattern Analysis of Basal Cell Nuclei for Oral Cancer Screening", *Bioinformatics and Biomedical Engineering (ICBBE)*, 2010 4th International conference on IEEE, Jun. 18, 2010, pp. 1-4.
Jusman et al., "Intelligent Screening Systems for Cervical Cancer", *The Scientific World Journal*, vol. 4115, No. 3, Jan. 1, 2014, pp. 1-15.
El-Sayed, "DNA ploidy and liver cell dysplasia in liver biopsies from patients with liver cirrhosis," *Canadian journal of gastroenterology*, vol. 18, p. 87-01, 2004.

(Continued)

*Primary Examiner* — G. Steven Vanni
(74) *Attorney, Agent, or Firm* — Brinks Gilson & Lione

(57) ABSTRACT

Disclosed is a cell analyzer comprising: a measuring device that includes a collecting section configured to collect target cells in a specimen with a filter, and is configured to measure the target cells collected by the collecting section; and a data processing device configured to analyze the target cells based on measurement data obtained by the measuring device, wherein the cell analyzer is operable in a first mode of measuring a clinical specimen collected from a subject and a second mode of measuring a quality control specimen containing particles having size capturable by the filter; and the data processing device is programmed to acquire an amount of particles collected by the collecting section based on measurement data of the quality control specimen obtained in the second mode, and output an alarm when the amount of particles meets a predetermined condition.

17 Claims, 21 Drawing Sheets

(56) References Cited

OTHER PUBLICATIONS

Gong, "Simultaneous analysis of cell cycle kinetics at two different DNA ploidy levels based on DNA content and cyclin B measurements," *Cancer Research*, vol. 53, p. 5096-5099, 1993.
Sysmex Corporation, "The 9$^{th}$ Technology Presentation," Obtained from the internet at <http://www.sysmex.co.jp/file.jsp?id=34136>, Mar. 16, 2012, 74 pages.
Van Leeuwen, A.M. et al., "The suitability of DNA cytometry for the prediction of the histological diagnosis in women with abnormal cervical smears," *British Journal of Obstetrics and Gynaecology*, Apr. 1996, vol. 103, pp. 359-365.
Office Action for U.S. Appl. No. 13/845,674, dated Aug. 10, 2015, 23 pages.
Office Action for U.S. Appl. No. 13/848,990, dated Aug. 12, 2015, 28 pages.
Office Action for U.S. Appl. No. 14/159,924, dated Aug. 11, 2015, 30 pages.
Filing Receipt for U.S. Appl. No. 14/508,522, filed Oct. 7, 2014, 3 pages.

\* cited by examiner

FIG. 8A
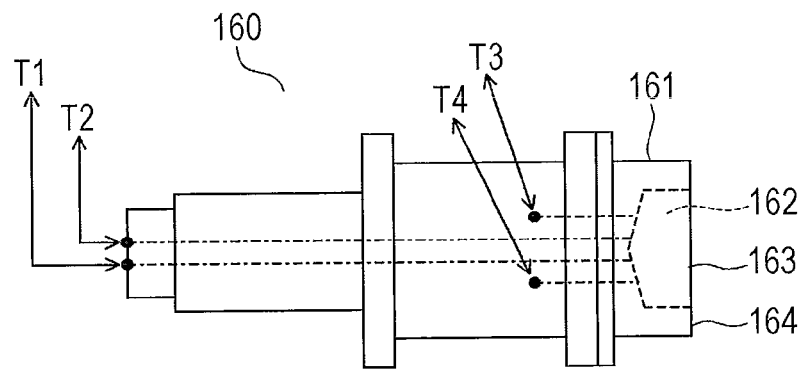
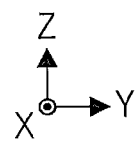
FIG. 8B
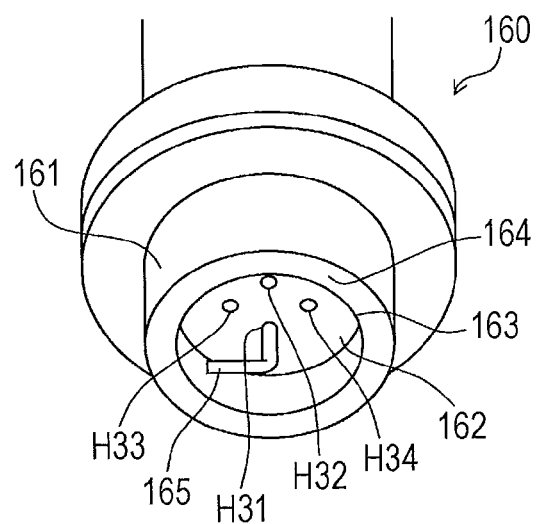

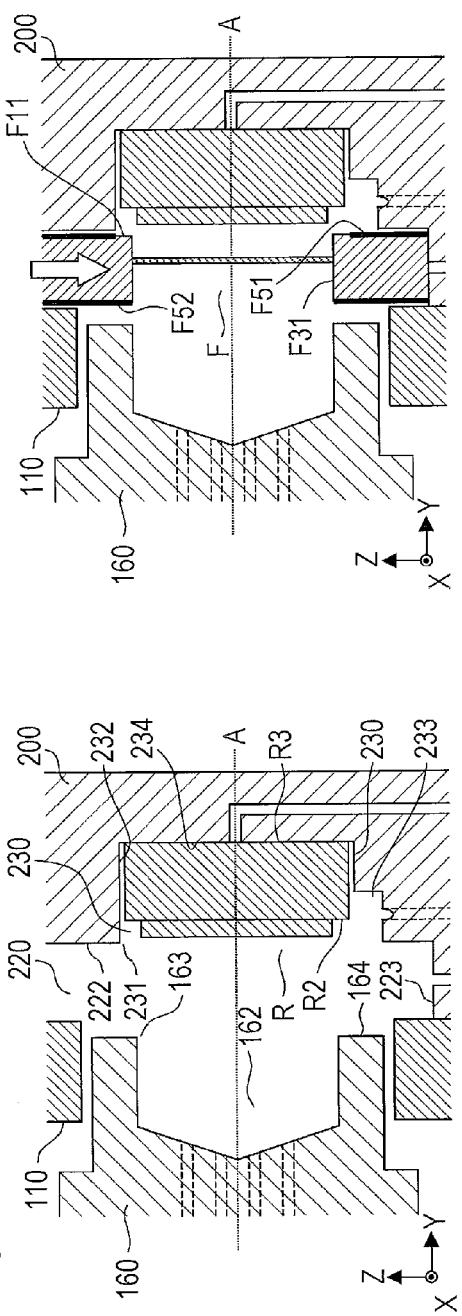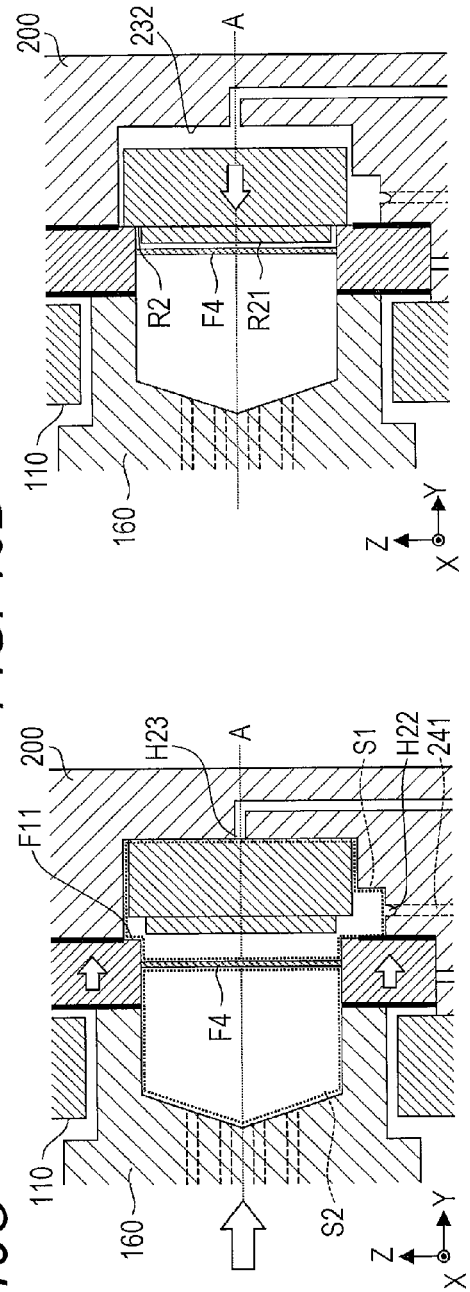

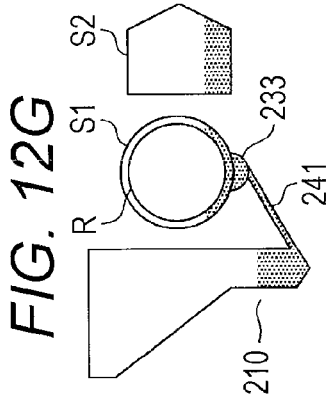 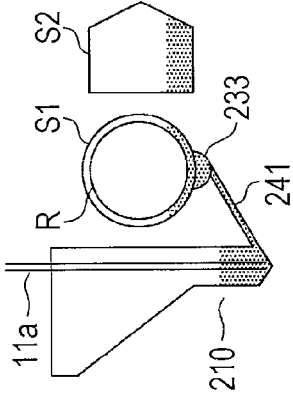 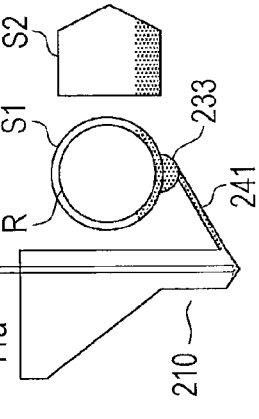
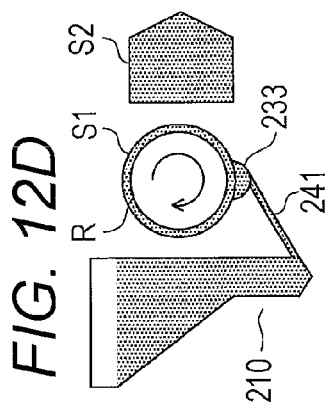 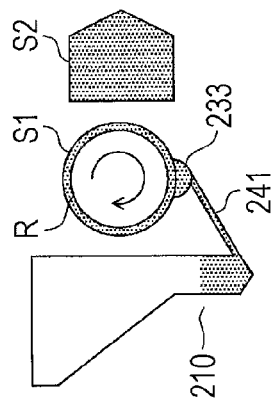 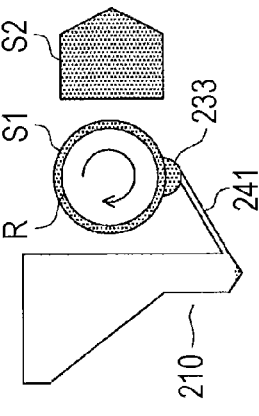
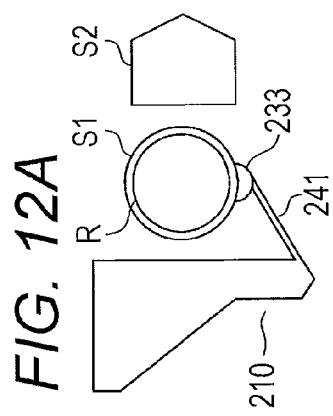 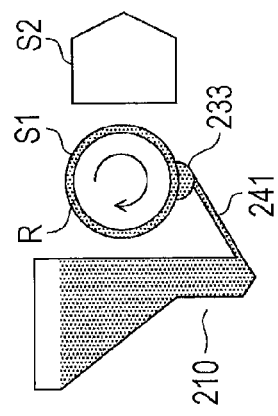 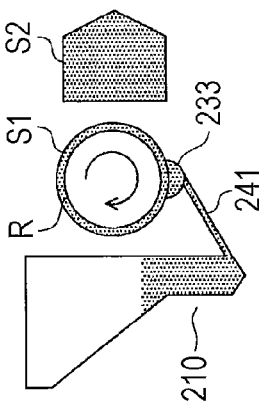

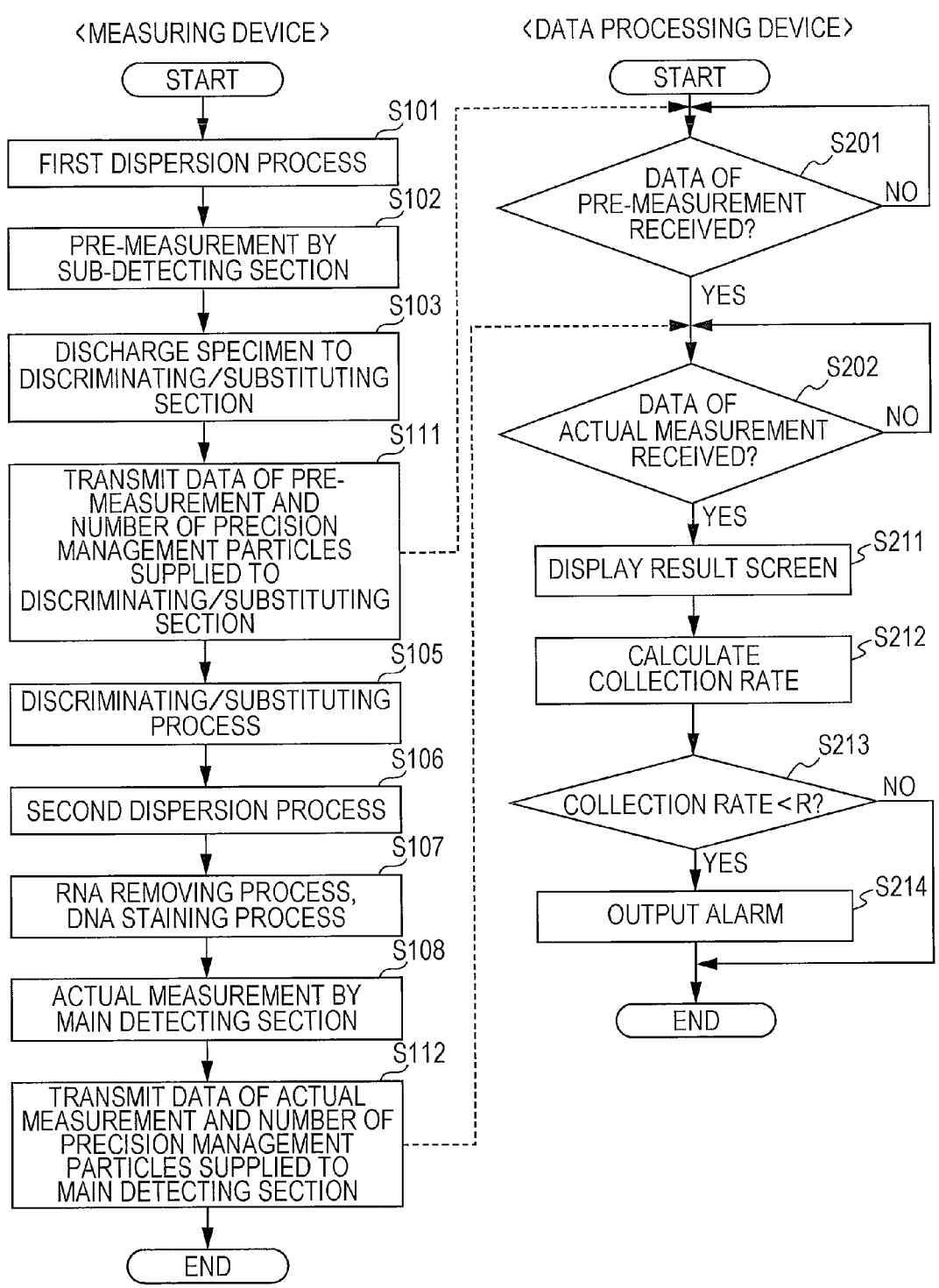

FIG. 17A

QUALITY CONTROL MEASUREMENT RESULT (D1)

| | X1 (D11) | X2 (D11) | Mean | | |
|---|---|---|---|---|---|
| 15u_PreFSCW_Mean | 40.0 | 60.0 | 50.0 | ch | ← i11 |
| 15u_PreFSCW_CV | 3.0 | 3.0 | 3.0 | % | ← i12 |
| 15u_PreFSCP_Mean | 2000.0 | 2000.0 | 2000.0 | ch | ← i13 |
| 15u_PreFSCP_CV | 3.0 | 3.0 | 3.0 | % | ← i14 |
| 15u_PreCount | 99999.9 | 99999.9 | 99999.9 | PIECES | ← i15 |
| 15u_FSCW_Mean | 40.0 | 40.0 | 40.0 | ch | ← i16 |
| 15u_FSCW_CV | 3.0 | 3.0 | 3.0 | % | ← i17 |
| 15u_FSCP_Mean | 2000.0 | 2000.0 | 2000.0 | ch | ← i18 |
| 15u_FSCP_CV | 3.0 | 3.0 | 3.0 | % | ← i19 |
| Collection Rate | 10.2 | 7.0 | 8.6 | % | ← i20 |
| | ↑ j1 | ↑ j2 | ↑ j3 | | [OK] |

FIG. 17B

ERROR LIST (D2, D21)

| Date Time | Level | Message |
|---|---|---|
| 2013/03/06 13:00:00 | STOP NEW ASPIRATION | QUALITY CONTROL ABNORMALITY 1 |
| 2013/03/06 13:00:00 | STOP NEW ASPIRATION | QUALITY CONTROL ABNORMALITY 2 |

ACTION (D22)
- THERE IS A PROBABILITY FILTER MAY HAVE PROBLEMS. REPLACE FILTER.
- CHECK MEASUREMENT RESULT AND CARRY OUT MEASUREMENT AGAIN, IF NECESSARY.
- IF ERROR REOCCURS, CONTACT CUSTOMER SUPPORT CENTER OR BRANCH OFFICE OR SALES BRANCH

[OK] [CANCEL]

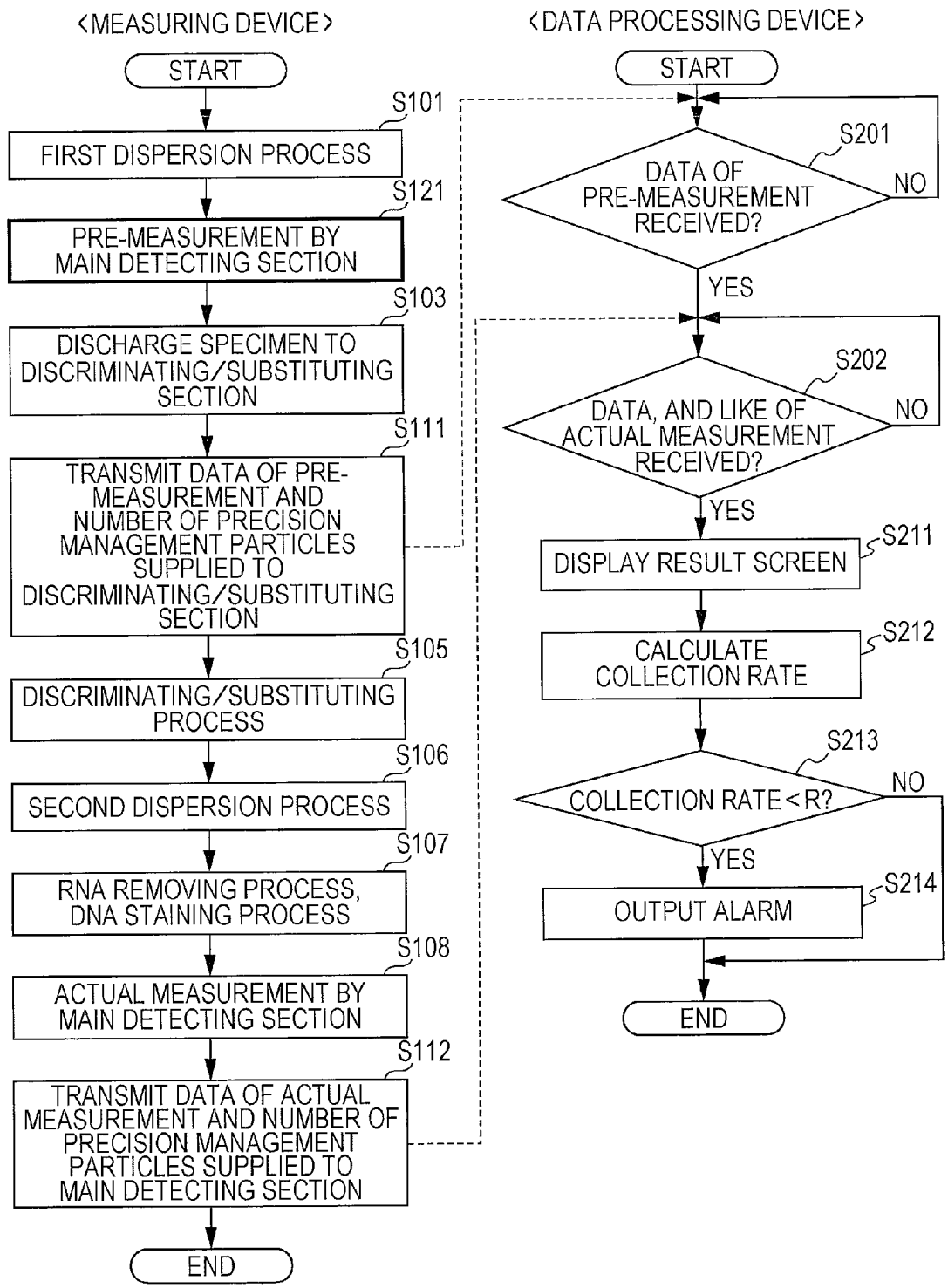

CELL ANALYZER, CELL COLLECTING APPARATUS, AND QUALITY CONTROL METHOD INCLUDING PROCESSING AND ANALYZING QUALITY CONTROL PARTICLES

RELATED APPLICATIONS

This application claims priority under 35 U.S.C. § 119 to Japanese Patent Application No. 2013-073549 filed on Mar. 29, 2013, the entire content of which is hereby incorporated by reference.

FIELD OF THE INVENTION

The present invention relates to a cell analyzer for collecting target cells in a specimen by a filter and analyzing them. The present invention also relates to a cell collecting apparatus, and a quality control method of the cell analyzer.

BACKGROUND OF THE INVENTION

There has been proposed a cell analyzer for analyzing cells contained in a biological specimen collected from a subject. WO 2006-103920 describes a cell analyzer for measuring, with a flow cytometer, epidermal cells contained in a specimen collected from a uterine cervix of a subject, and determining the progress status of canceration based on the measurement result.

In such cell analyzer, the analysis is carried out on the individual cell, and thus the number of cells to be analyzed is desirably large in order to increase the analysis precision. US 2011-076755 A describes a cell analyzer enabled to concentrate cells in the specimen for increasing the number of cells to be analyzed while suppressing the amount of specimen. A filter is used in the cell analyzer for discriminating the cells to be measured.

Since the filter is a consumable supply, it needs to be replaced after being used for a number of times. However, if the attachment of the filter is not adequate or if the filter is damaged, the target cell cannot be appropriately discriminated. In such a case, the abnormality of the filter is to be desirably recognized by the user.

SUMMARY OF THE INVENTION

A first aspect of the present invention a cell analyzer comprising: a measuring device that includes a collecting section configured to collect target cells in a specimen with a filter, and is configured to measure the target cells collected by the collecting section; and a data processing device configured to analyze the target cells based on measurement data obtained by the measuring device, wherein the cell analyzer is operable in a first mode of measuring a clinical specimen collected from a subject and a second mode of measuring a quality control specimen containing particles having size capturable by the filter; and the data processing device is programmed to acquire an amount of particles collected by the collecting section based on measurement data of the quality control specimen obtained in the second mode, and output an alarm when the amount of particles meets a predetermined condition.

A second aspect of the present invention is a cell collecting apparatus comprising: a filter provided with pores; a specimen supplying section configured to supply a specimen to the filter; a collecting section configured to collect particles captured by the filter; a detecting section configured to detect particles collected by the collecting section; and a data processing device programmed to cause the specimen supplying section to supply a quality control specimen containing particles of size capturable by the filter, cause the collecting section to collect the particles of the quality control specimen captured by the filter, cause the detecting section to detect the collected particles, acquire an amount of particles detected by the detecting section, and output an alarm when the amount of particles meets a predetermined condition.

A third aspect of the present invention is a quality control method of a cell analyzer including a filter, a measuring section and a outputting section, the method comprising: supplying a quality control specimen containing a known amount of particles to the filter, wherein the filter is provided with pores of size capable of capturing the particles; measuring, by the measuring section, an amount of the particles captured by the filter; outputting, by the outputting section, an alarm of urging a replacement of the filter when the amount of particles captured by the filter meets a predetermined condition.

BRIEF DESCRIPTION OF THE DRAWINGS

FIG. 8A is a side view showing a configuration of a piston according to the embodiment;

FIG. 8B is a perspective view showing a configuration of the piston according to the embodiment;

FIG. 10A to FIG. 10D are views showing the procedure of installing the filter member according to the embodiment;

FIG. 12A to FIG. 12I are views schematically showing the state of liquid in an accommodating unit and a space according to the embodiment;

FIG. 16 is a flowchart showing processes of the cell analyzer in a quality control measurement mode according to the embodiment;

FIG. 17A is a view showing a result screen according to the embodiment;

FIG. 17B is a view showing an error list screen according to the embodiment;

FIG. 19 is a flowchart showing processes of the cell analyzer in the quality control measurement mode according to a second variant;

DETAILED DESCRIPTION OF THE PREFERRED EMBODIMENTS

In the present embodiment, the present invention is applied to a cell analyzer configured to prepare a measurement specimen including cells in a clinical specimen collected from a subject (patient) and to acquire information associated with canceration of cells based on the prepared measurement specimen. A cell analyzer 1 according to the present embodiment will be hereinafter described with reference to the drawings.

Figure 1:
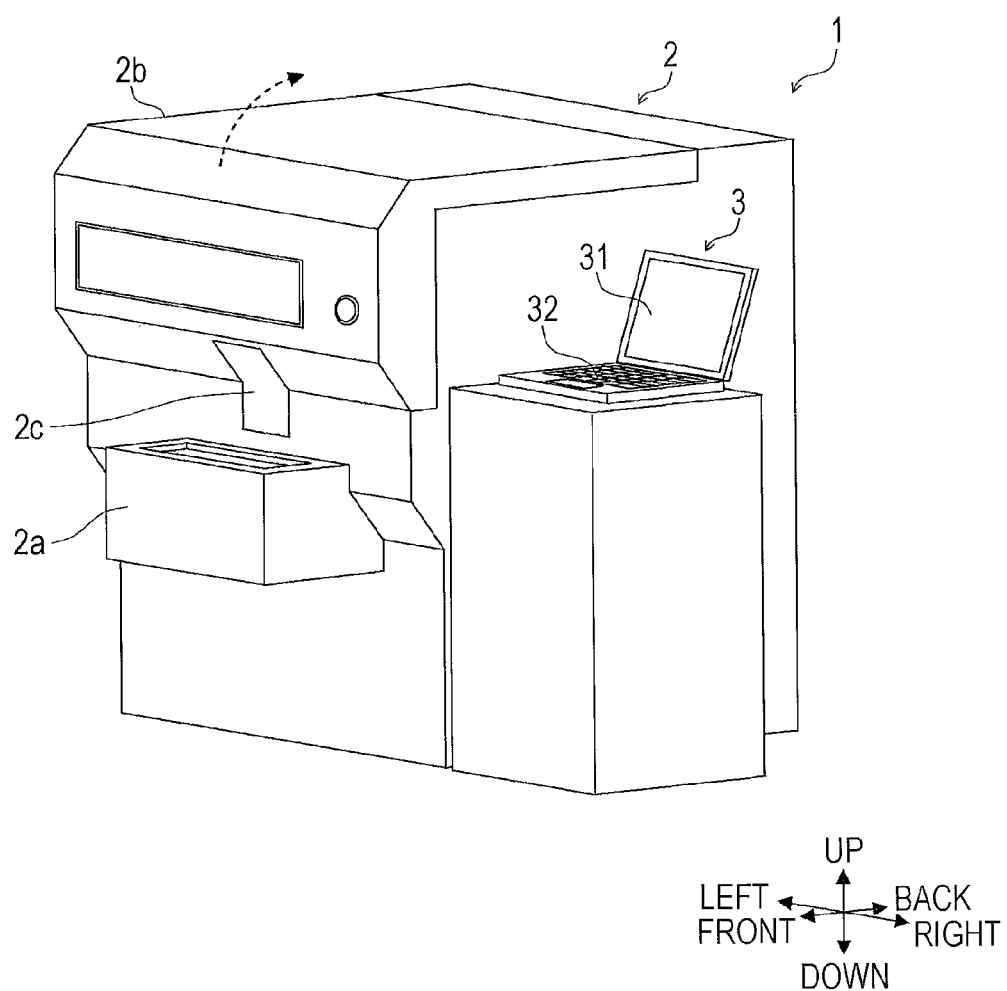
FIG. 1 is a view showing a configuration of an outer appearance of a cell analyzer according to an embodiment.

FIG. 1 is a view showing a configuration of an outer appearance of the cell analyzer 1.

The cell analyzer 1 flows a measurement specimen containing cells (hereinafter referred to as "analyzing target cell") collected from a subject through a flow cell, and irradiates the measurement specimen flowing through the flow cell with a laser light. Forward scattered light, side scattered light, fluorescence occurred from the particles in the measurement specimen are detected and light signals thereof are analyzed, thus determining whether or not the cells contain cancer cells or cells in progress of canceration. In the following embodiment, the analyzing target cell analyzed by the cell analyzer 1 is an epidermal cell of the uterine cervix collected from the subject. The cell analyzer 1 is used for screening the uterine cervical cancer.

The cell analyzer 1 includes a measuring device 2 configured to perform measurement, and the like of the analyzing target cell, and a data processing device 3 connected to the measuring device 2 and configured to perform analysis, and the like of the measurement data. On a front surface of the measuring device 2 is installed a sample setting section 2a for setting a plurality of specimen containers 4 (see FIG. 2), each of which contains a mixed solution (specimen) of a preservative solution having methanol as the main component and a cell collected from the uterine cervix of the subject. A cover 2b is arranged on the measuring device 2, and the user opens the cover 2b upward to access the inside of the measuring device 2. An opening 2c through which a sample pipette section 11, to be described later, is inserted and removed is arranged in the measuring device 2. The data processing device 3 includes a display section 31 configured to display an analysis result, and the like, and an input section 32 configured to receive an instruction from the user.

Figure 2:
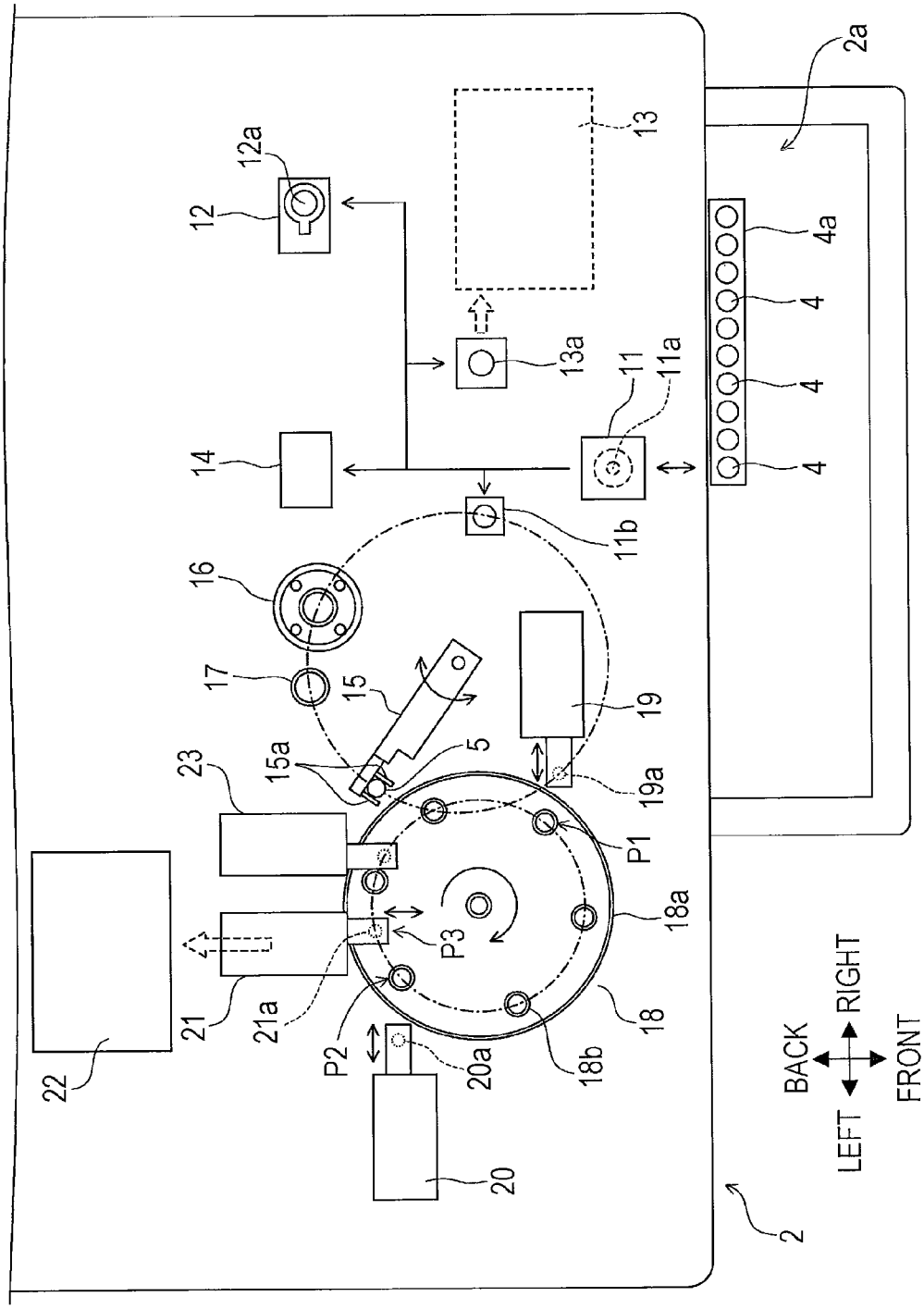
FIG. 2 is a plan view showing an internal configuration of a measuring device according to the embodiment.

FIG. 2 is a plan view showing an internal configuration of the measuring device 2.

The sample setting section 2a sequentially transports a rack 4a, on which a plurality of specimen containers 4 is set, up to an aspirating position of the specimen by the sample pipette section 11. The sample pipette section 11 includes a pipette 11a extending in a vertical direction, and is configured to aspirate and discharge the specimen by moving the pipette 11a in the horizontal direction and the vertical direction.

When the specimen container 4 is positioned at the aspirating position of the sample setting section 2a, the specimen contained in the specimen container 4 is aspirated by the sample pipette section 11, and discharged to a specimen accommodating portion 12a of a first dispersion section 12. The first dispersion section 12 disperses aggregating cells contained in the specimen by applying a shear force. A part of the specimen, in which the process (first dispersion process) by the first dispersion section 12 is completed, is aspirated by the sample pipette section 11, and discharged to a specimen take-in portion 13a of a sub-detecting section 13. The sub-detecting section 13 includes a flow cytometer 40, and performs the measurement of the specimen (hereinafter referred to as "pre-measurement") before the process by the discriminating/substituting section 14, to be described later.

Figure 3A:
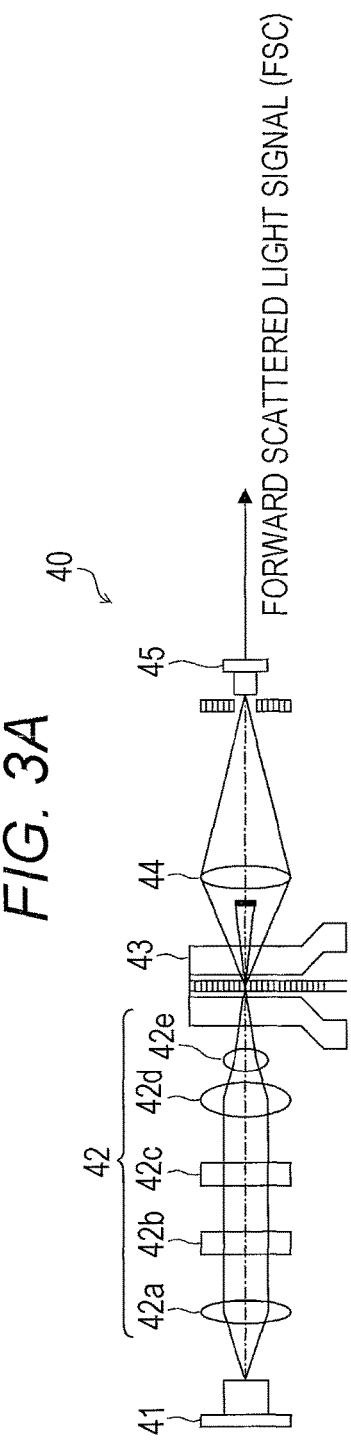
FIG. 3A is a side view showing a configuration of a flow cytometer according to the embodiment.

FIG. 3A is a view showing a configuration of the flow cytometer 40 of the sub-detecting section 13.

The specimen discharged to the specimen take-in portion 13a is supplied to a flow cell 43, and the laser light exit from the semiconductor laser 41 is collected on the specimen flowing through the flow cell 43 by a lens system 42 including a plurality of lenses. The lens system 42 is configured by a collimator lens 42a, a cylinder lens system including plano-convex cylinder lens 42b and biconcave cylinder lens 42c, and a condenser lens system including condenser lens 42d and condenser lens 42e.

The light collecting lens 44 collects the forward scattered light generated by the cells in the specimen at a scattered light detector including a photodiode 45. The photodiode 45 converts the received light signal to an electric signal, and outputs the forward scattered light signal (FSC). The FSC is amplified by a pre-amplifier (not shown) and output to a signal processing section 27 (see FIG. 13) of the measuring device 2.

Returning back to FIG. 2, the number of analyzing target cells contained in the specimen supplied to the sub-detecting section 13 is acquired based on the FSC acquired by the pre-measurement, and the concentration of the analyzing target cell contained in the specimen supplied to the sub-detecting section 13 is calculated based on the acquired number of analyzing target cells. The amount (volume) of specimen to be supplied to the discriminating/substituting section 14 is determined based on the calculated concentration. The specimen accommodated in the specimen accommodating portion 12a of the first dispersion section 12 is aspirated by the volume determined as above by the sample pipette section 11, and the aspirated specimen is discharged to an accommodating unit 210 (see FIG. 6A) of the discriminating/substituting section 14. A predetermined number of analyzing target cells are accommodated in the accommodating unit 210.

The discriminating/substituting section 14 substitutes the preservative solution having methanol contained in the specimen as the main component with diluted solution. In other words, the discriminating/substituting section 14 executes the process of diluting the concentration of methanol contained in the specimen using the diluted solution so that the cell staining process in the post-step can be suitably carried out. Tris-HCl (tris buffer) is used for the diluted solution. The discriminating/substituting section 14 discriminates the analyzing target cell (epidermal cell of uterine cervix) contained in the specimen, and the other cells such as red blood cells, white blood cells, bacteria and foreign substances. The concentrated solution in which the analyzing target cell is concentrated so as to include number of cells necessary for detecting the cancer cell is thereby obtained. The detailed configuration of the discriminating/substituting section 14 will be described later.

The specimen container 5 set in a holder 18b of a reaction section 18 is gripped by a scissor-shaped grip portion 15a of a container transfer section 15, and positioned at a specimen hand-over portion 11b. Subsequently, the concentrated solution accommodated in the accommodating unit 210 of the discriminating/substituting section 14 is aspirated by the sample pipette section 11, and discharged to the specimen container 5 positioned at the specimen hand-over portion 11b. The container transfer section 15 transfers the specimen container 5 to a second dispersion section 16.

The second dispersion section 16 applies an ultrasonic vibration to the specimen concentrated in the discriminating/substituting section 14. The aggregating cells remaining after the first dispersion process are dispersed to a single cell. The specimen container 5, in which the process (second dispersion process) by the second dispersion section 16 is completed, is set in a liquid removing section 17 by the container transfer section 15. The liquid removing section 17 removes (drains) the liquid attached to the outer surface of the specimen container 5. The specimen container 5, in which the process by the liquid removing section 17 is completed, is set in the holder 18b of the reaction section 18 by the container transfer section 15.

The reaction section 18 warms the specimen container 5 set in the holder 18b to a predetermined temperature (about 37 degrees), and advances the reaction between the specimen in the specimen container 5 and the reagent added by a first reagent adding section 19 and a second reagent adding section 20. The reaction section 18 includes a circular rotation table 18a configured to be rotatable, where a plurality of holders 18b are arranged on an outer circumferential portion of the rotation table 18a so that the specimen container 5 can be set therein.

The first reagent adding section 19 and the second reagent adding section 20 respectively includes a supplying portion 19a, 20a movable to the positions P1, P2 above the specimen container 5 set in the rotation table 18a. The first reagent adding section 19 and the second reagent adding section 20 respectively adds a predetermined amount of reagent from the supplying portion 19a, 20a into the specimen container 5 when the specimen container 5 is transported to the positions P1, P2 by the rotation table 18a.

The reagent added by the first reagent adding section 19 is RNase for performing the RNA removing process on the cell, and the reagent added by the second reagent adding section 20 is a stain solution for performing the DNA staining process on the cell. According to the RNA removing process, the RNA in the cell is decomposed, so that only the DNA of the cell nucleus can be measured. The DNA staining process is carried out by propidium iodide (PI), which is the fluorescence stain solution containing pigment. The staining is selectively performed on the nucleus in the cell by the DNA staining process. The fluorescence from the nucleus can be detected.

A specimen aspirating section 21 includes a pipette 21a movable to a position P3 above the specimen container 5 set in the rotation table 18a, and aspirates the specimen (measurement specimen) added with the reagent in the specimen container 5 when the specimen container 5 is transported to the position P3 by the rotation table 18a. The specimen aspirating section 21 supplies a measurement specimen aspirated by the pipette 21a to a main detecting section 22 through a flow path (not shown). The main detecting section 22 includes a flow cytometer 50, and performs the measurement (hereinafter referred to as "actual measurement") of the measurement specimen prepared in the above manner.

Figure 3B:
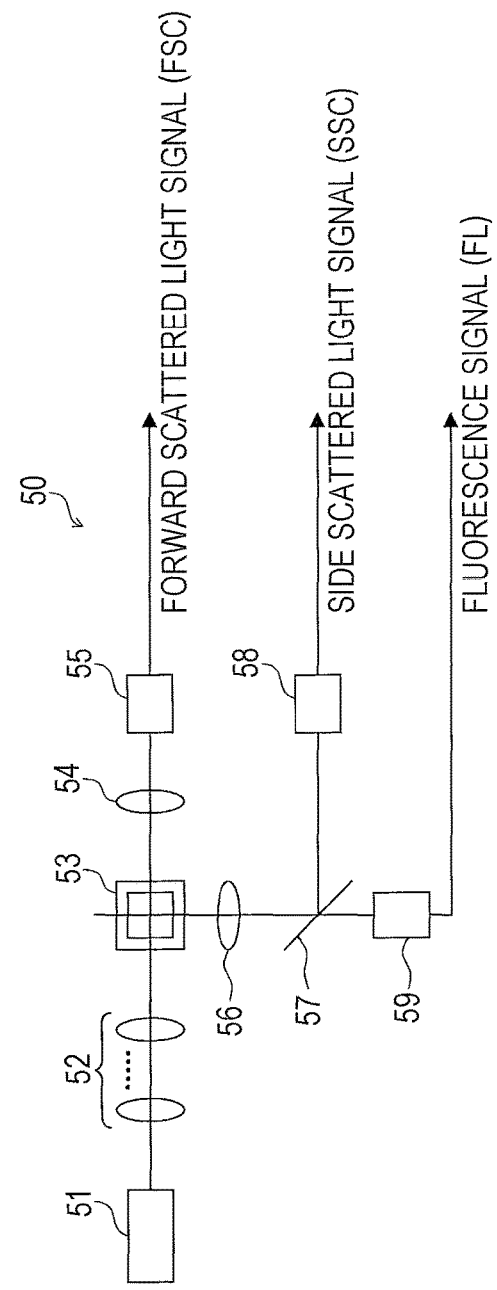
FIG. 3B is a plan view showing the configuration of the flow cytometer.

FIG. 3B is a view showing a configuration of the flow cytometer 50 of the main detecting section 22.

The semiconductor laser 51, the lens system 52, the flow cell 53, the light collecting lens 54, and the photodiode 55 are similar to the configuration shown in FIG. 3A. In other words, the measurement specimen aspirated by the pipette 21a of the specimen aspirating section 21 is supplied to the flow cell 53, and the laser light exit from the semiconductor laser 51 is collected at the measurement specimen flowing through the flow cell 53. The photodiode 55 converts the received light signal to an electric signal, and outputs the forward scattered light signal (FSC).

The light collecting lens 56 collects the side scattered light and the fluorescence generated by the analyzing target cell and the nucleus in such cell, and introduces the same to a dichroic mirror 57. The dichroic mirror 57 reflects the side scattered light toward a photomultiplier 58, and transmits the fluorescence toward a photomultiplier 59. The side scattered light is collected at the photomultiplier 58, and the fluorescence is collected at the photomultiplier 59. The photomultipliers 58, 59 convert the received light signal to an electric signal, and respectively output the side scattered light signal (SSC) and the fluorescence signal (FL). The FSC, the SSC, and the FL are amplified by a pre-amplifier (not shown), and output to a signal processing section 24 (see FIG. 13) of the measuring device 2.

Returning back to FIG. 2, the number of analyzing target cells contained in the measurement specimen supplied to the main detecting section 22 is detected similar to the case of the pre-measurement based on the FSC acquired by the actual measurement. The determination on the canceration of the analyzing target cells is carried out in the data processing device 3 based on the FSC, the SSC, and the FL acquired by the actual measurement. A container washing section 23 discharges washing liquid into the specimen container 5 set in the rotation table 18a to wash the interior of the specimen container 5 of after the measurement specimen is supplied to the main detecting section 22 by the specimen aspirating section 21.

Figure 4:
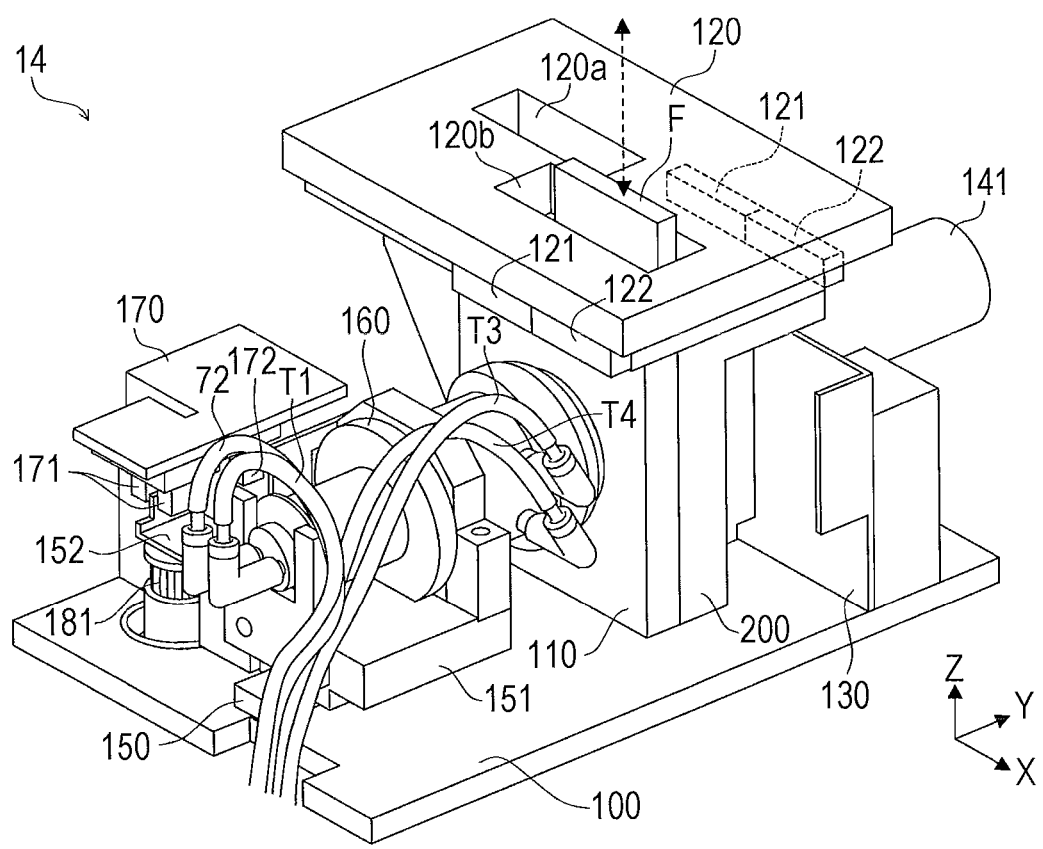
FIG. 4 is a view showing a configuration of a discriminating/substituting section according to the embodiment.

FIG. 4 is a view showing a configuration of the discriminating/substituting section 14. In FIG. 4, the Z-axis direction is the vertical direction, and the positive direction of the Z-axis and the negative direction of the Z-axis are upward direction and downward direction, respectively.

A base 100 is a plate-shaped member parallel to the XY plane. An accommodating body 200, supporting members 110, 130, 170, and a rail 150 are installed on the base 100. In addition, various mechanisms, and the like are installed on the base 100, but the illustration of such mechanisms, and the like is omitted in FIG. 4 for the sake of convenience.

The supporting member 110 is a plate-shaped member parallel to the XZ plane, where a hole 111 (see FIG. 9) that passes through in the Y-axis direction is formed in the supporting member 110. The upper plate 120 is installed on the upper surfaces of the accommodating body 200 and the supporting member 110. The upper plate 120 is positioned in the measuring device 2 such that the user can access the upper plate 120 when the cover 2b (see FIG. 1) of the measuring device 2 is opened upward.

The upper plate 120 is formed with holes 120a, 120b passing in the up and down direction. The pipette 11a of the sample pipette section 11 performs aspiration and discharging of specimen with respect to the accommodating unit 210 of the accommodating body 200, to be described later, through the hole 120a. The user opens the cover 2b provided on the measuring device 2 to install and take out the filter member F with respect to the accommodating unit 220 of the accommodating body 200, to be described later, through the hole 120b along the broken arrow (vertical direction).

The upper plate 120 is a member having translucency, where sensors 121, 122 including the light emitting portion and the light receiving portion are installed on the upper plate 120. When the filter member F is correctly installed, the light emitted from the light emitting portion of the sensor 121 is shielded by the filter member F, and the light emitted from the light emitting portion of the sensor 122 is passed through a cutout F6 (see FIGS. 7A, 7B) of the filter member F. When the filter member F is installed with the surfaces F1, F2 (see FIGS. 7A, 7B) of the filter member F reversed, the light emitted from the light emitting portions of the sensors 121, 122 is shielded by the filter member F. Whether or not the filter member F is correctly set thus can be detected.

The supporting member 130 supports the motor 141. The supporting member 151 is installed to be slidably movable in the Y-axis direction on the rail 150. A flange part 152 and a piston 160 are installed on the supporting member 151, and tubes T1 to T4 are connected to the piston 160. Sensors 171, 172 including the light emitting portion and the light receiving portion are installed on the supporting member 170.

Figure 5A:
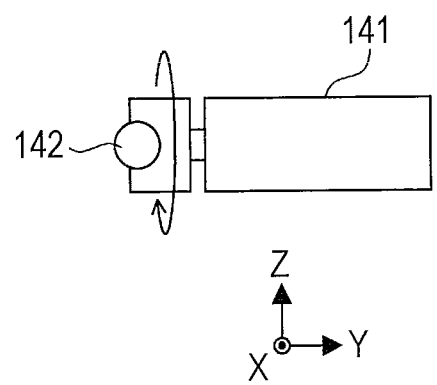
FIG. 5A is a side view of a motor according to the embodiment.

FIG. 5A is a side view of the motor 141. The rotation axis of the motor 141 is parallel to the Y-axis, and coincides with the center axis A, to be described later. A magnet 142 is installed on the distal end on the negative direction side of the Y-axis of the motor 141. When the motor 141 is driven and the magnet 142 is rotated within the XZ plane, the stirrer R, to be described later, is rotated through the wall of the accommodating body 200.

Figure 5B:
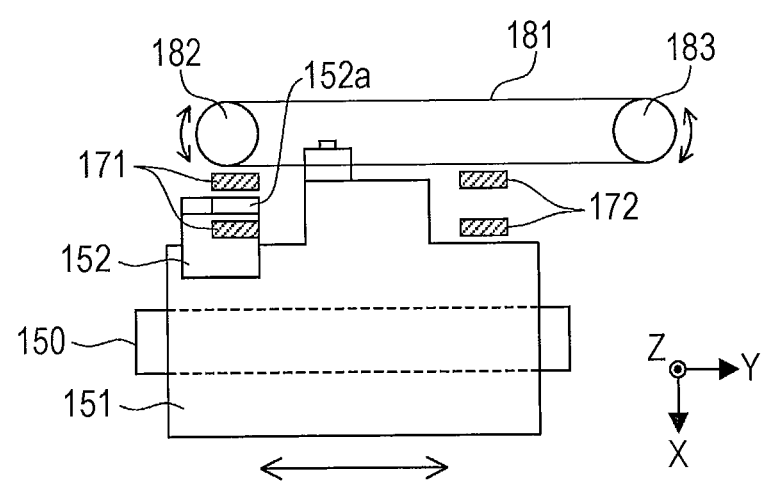
FIG. 5B is a plan view when a mechanism for driving a piston according to the embodiment is seen from above.

FIG. 5B is a plan view of when the mechanism for driving the piston 160 is seen from above. In FIG. 5B, the illustration of the piston 160 is omitted for the sake of convenience. The supporting member 151 is fixed to a belt 181. The belt 181 is supported by pulleys 182, 183. The pulley 182 is connected to the rotation shaft of the stepping motor installed on the lower surface side of the base 100. When the stepping motor is driven, the supporting member 151 is slidably moved in the Y-axis direction on the rail 150, and the piston 160 is driven in the Y-axis direction. The sensors 171, 172 are installed at positions where a light shielding portion 152a of a flange part 152 installed on the supporting member 151 can be detected. It can be detected that the piston 160 is positioned on the leftmost side and positioned on the rightmost side by the detection signals of the sensors 171, 172.

Figure 6A:
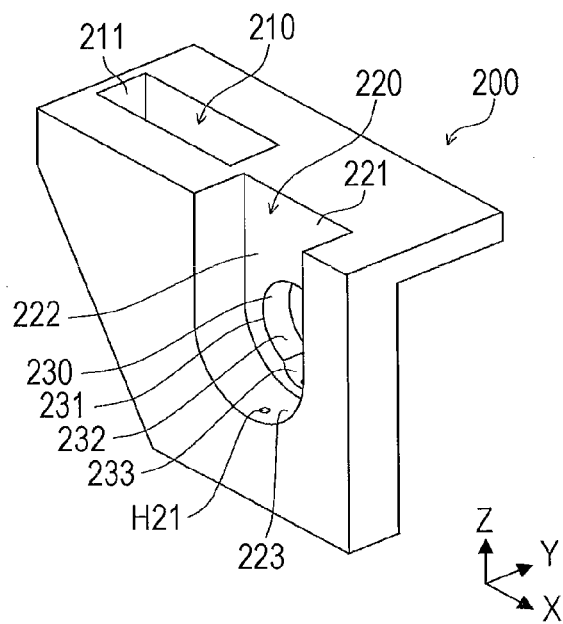
FIG. 6A is a view showing a configuration of an accommodating body according to the embodiment.
Figure 6B:
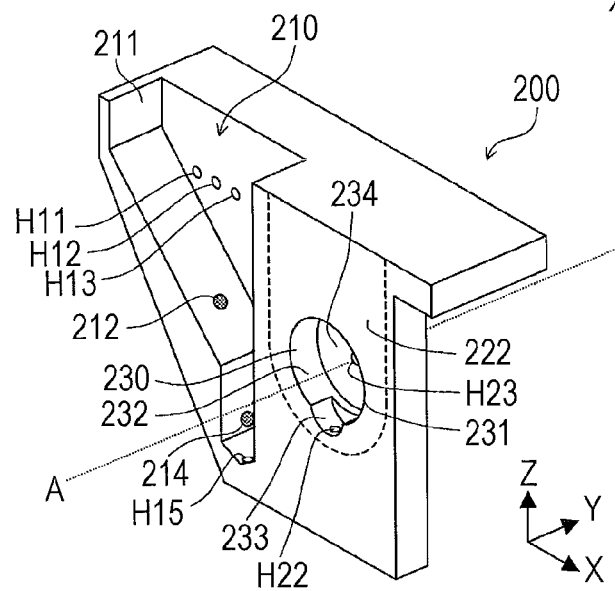
FIG. 6B is a view showing a state in which the accommodating body according to the embodiment is cut.
Figure 6C:
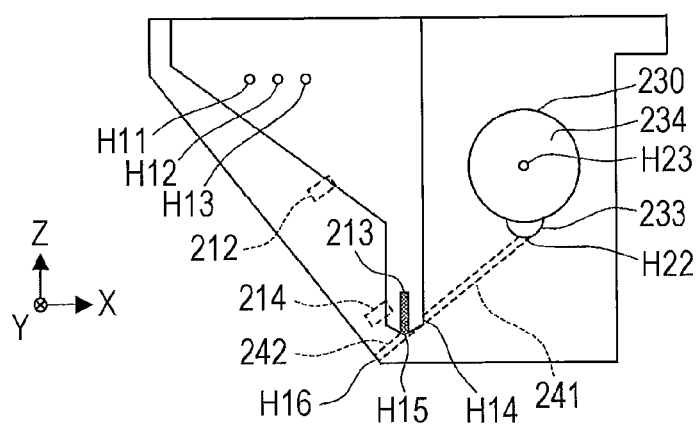
FIG. 6C is a side view of the accommodating body according to the embodiment.

FIG. 6A is a view showing a configuration of the accommodating body 200. FIG. 6B is a view showing a state in which the accommodating body 200 is cut along a plane including a wall portion 222 in FIG. 6A. FIG. 6C is a side view when the accommodating body 200 shown in FIG. 6B is seen in the positive direction of the Y-axis.

With reference to FIG. 6A, the accommodating units 210, 220 are formed in the accommodating body 200. An insertion port 211 positioned at the upper part of the accommodating unit 210 is connected to a hole 120a of the upper plate 120, and an insertion port 221 positioned at the upper part of the accommodating unit 220 is connected to a hole 120b of the upper plate 120. The accommodating unit 220 includes the wall portion 222 parallel to the XZ plane, where the wall portion 222 is formed with a recess 230 to which the stirrer R, to be described later, is accommodated. A bottom surface 223 of the accommodating unit 220 has a curved surface, and a hole H21 is formed at the lowermost position of the bottom surface 223. The negative direction side of the Y-axis of the accommodating unit 220 is opened.

With reference to FIGS. 6B and 6C, the recess 230 includes an opening 231 that opens the recess 230 toward the negative direction of the Y-axis, an inner side surface 232 that is circular when seen in the Y-axis direction, a retaining portion 233 formed on the lower side of the inner side surface 232, and a wall portion 234 parallel to the XZ plane. The recess 230 is spaced apart from the accommodating unit 210 in plan view, that is, in a direction (horizontal direction) within the XY plane. The center axis A shown with a dotted line in FIG. 6B is an axis that passes through the circular center of when the inner side surface 232 is seen in the Y-axis direction and that is parallel to the Y-axis direction. The retaining portion 233 is formed in the inner side surface 232 so as to be recessed in a direction of separating from the center axis A. A hole H22 is formed at the lowermost position of the retaining portion 233. A hole H23 is formed in the wall portion 234 at a position where the center axis A intersects with the wall portion 234.

The accommodating unit 210 has a shape in which the interior gradually narrows in the depth direction (downward direction). Holes H11 to H13 are formed at the upper part of the inner side surface of the accommodating unit 210, and holes H14, H15 are formed at the deepest part of the accommodating unit 210. The hole H14 is connected to the hole H22 of the retaining portion 233 through a flow path 241, and the hole H15 is connected to the hole H16 formed in an outer surface of the accommodating body 200 through a flow path 242. The arrangement of the accommodating unit 210, the recess 230, and the flow path 241 is adjusted such that the hole H14 becomes lower than the hole H22. The hole H16 is connected to a valve V25 (see FIG. 11), and the diameter of the flow path 242 is sufficiently small. Thus, the specimen accommodated in the accommodating unit 210 does not flow toward the lower side than the hole H15.

Pins 212 to 214 are installed in the accommodating unit 210. The pins 212 to 214 are connected to a resistance type liquid level sensor unit 293 (see FIG. 13). The liquid level sensor unit 293 detects whether or not the liquid level in the accommodating unit 210 is higher than the height position of the pin 212 based on a current-flowing state of the pins 212, 214, and detects whether or not the liquid level in the accommodating unit 210 is higher than the height position of the upper part of the pin 213 based on the current-flowing state of the pins 213, 214.

Figure 7A:
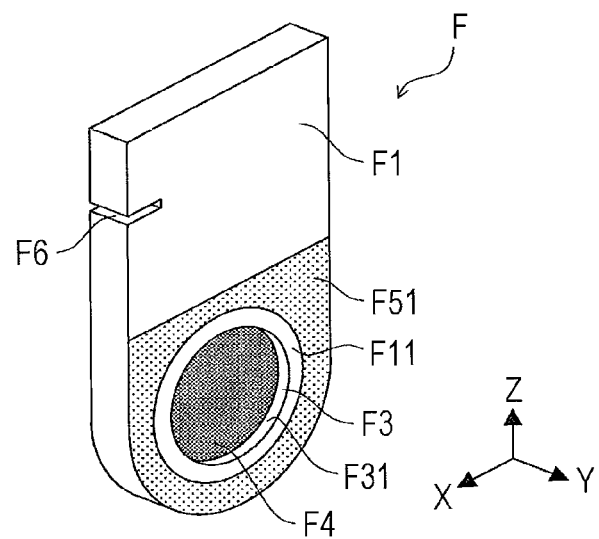
FIG. 7A and FIG. 7B are views showing a configuration of a filter member according to the embodiment.
Figure 7B:
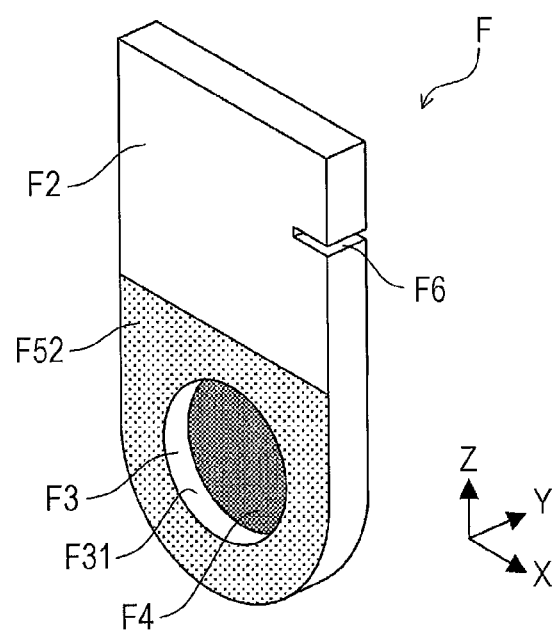

FIGS. 7A and 7B are views showing a configuration of the filter member F. FIGS. 7A and 7B also show the coordinate axis of when the filter member F is appropriately set with respect to the accommodating unit 220.

The filter member F includes surfaces F1, F2 parallel to the XZ plane, a hole F3 that passes through the filter member F in the Y-axis direction, a filter F4, a thin-film like rubber F51 installed on the surface F1, and a thin-film like rubber F52 installed on the surface F2. The surfaces F1, F2 are positioned on the positive direction side of the Y-axis and the negative direction side of the Y-axis, respectively. The hole F3 has a tubular inner side surface F31. The filter F4 is installed such that the filtering surface is parallel to the XZ plane with respect to the inner side surface F31 of the hole F3. The filter F4 is provided with a plurality of pores each having a diameter that allows cells smaller than the analyzing target cells, such as red blood cells, white blood cells, bacteria, and foreign substances to pass through, but does not allow the analyzing target cells (epidermal cells of the uterine cervix) to pass through. In the present embodiment, the diameter of the hole of the filter F4 is set to 10 μm. Furthermore, the distance between the filter F4 and the surface F1 is smaller than the distance between the filter F4 and the surface F2 in the Y-axis direction. The rubber F51 is installed at the periphery of the opening on the surface F1 side of the hole F3, and a surface F1, which is a part of the surface F1, is exposed between the opening on the surface F1 side of the hole F3 and the rubber F51. The rubber F52 is installed at the periphery of the opening on the surface F2 side of the hole F3.

Figure 7C:
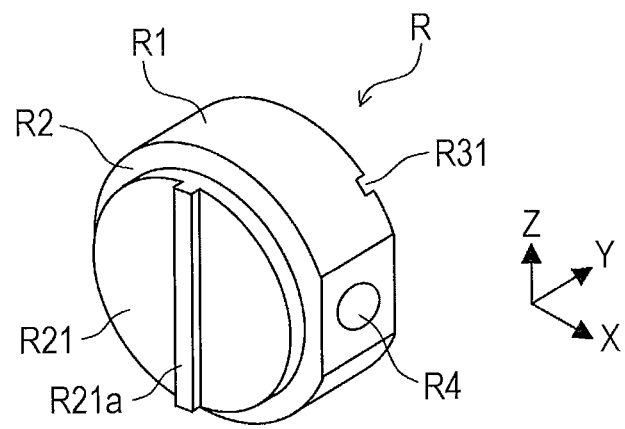
FIG. 7C and FIG. 7D are views showing a configuration of a stirrer according to the embodiment.
Figure 7D:
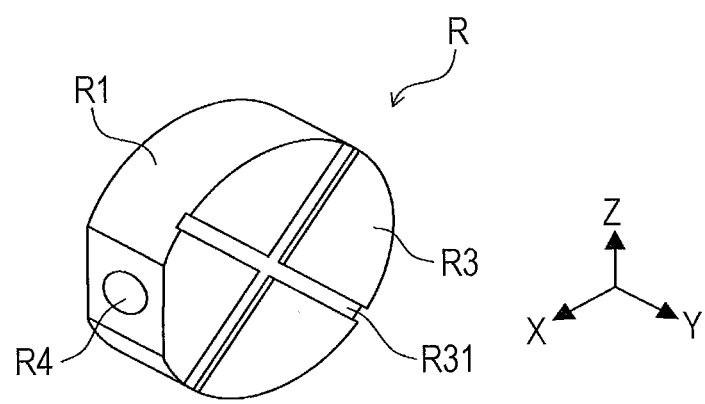

FIGS. 7C and 7D are views showing a configuration of the stirrer R. FIGS. 7C and 7D also show the coordinate axis of when the stirrer R is accommodated in the recess 230.

The stirrer R includes a body portion R1 having a tubular shape, surfaces R2, R3 parallel to the XZ plane, and a magnet R4. The surfaces R2, R3 are positioned on the negative direction side of the Y-axis and the positive direction side of the Y-axis, respectively. A tubular projection R21 that projects out in the negative direction side of the Y-axis with respect to the surface R2 is formed on the surface R2, and the diameter of the projection R21 is smaller than the diameter of the outer circumference of the surface R2. A flange part R21a is further formed on the projection R21. A groove R31 that intersects at the center of the surface R3 is formed in the surface R3. The magnet R4 is installed to pass the center of the stirrer R and pass through the stirrer R within the XZ plane. Thus, the stirrer R rotates around the Y-axis as the center when the magnet 142 shown in FIG. 5A is rotated by the motor 141.

FIGS. 8A and 8B are a side view and a perspective view, respectively, showing the configuration of the piston 160.

The piston 160 includes a distal end 161 having a circular column shape in the positive direction side of the Y-axis. On the positive direction side of the Y-axis of the distal end 161 is formed a recess 162, an opening 163 that opens the recess 162 in the positive direction side of the Y-axis, and a surface 164. Holes H31 to H34 are formed on the surface on the negative direction side of the Y-axis of the recess 162, and the holes H31 to H34 are connected to the tubes T1 to T4 through a flow path arranged inside the piston 160. An L-shaped pipe 165 is connected to the hole H31, and the distal end of the pipe 165 is positioned at the upper part (positive direction side of the Z-axis) in the recess 162. The surface 164 is parallel to the XZ plane, and is formed at the periphery of the opening 163.

Figure 9:
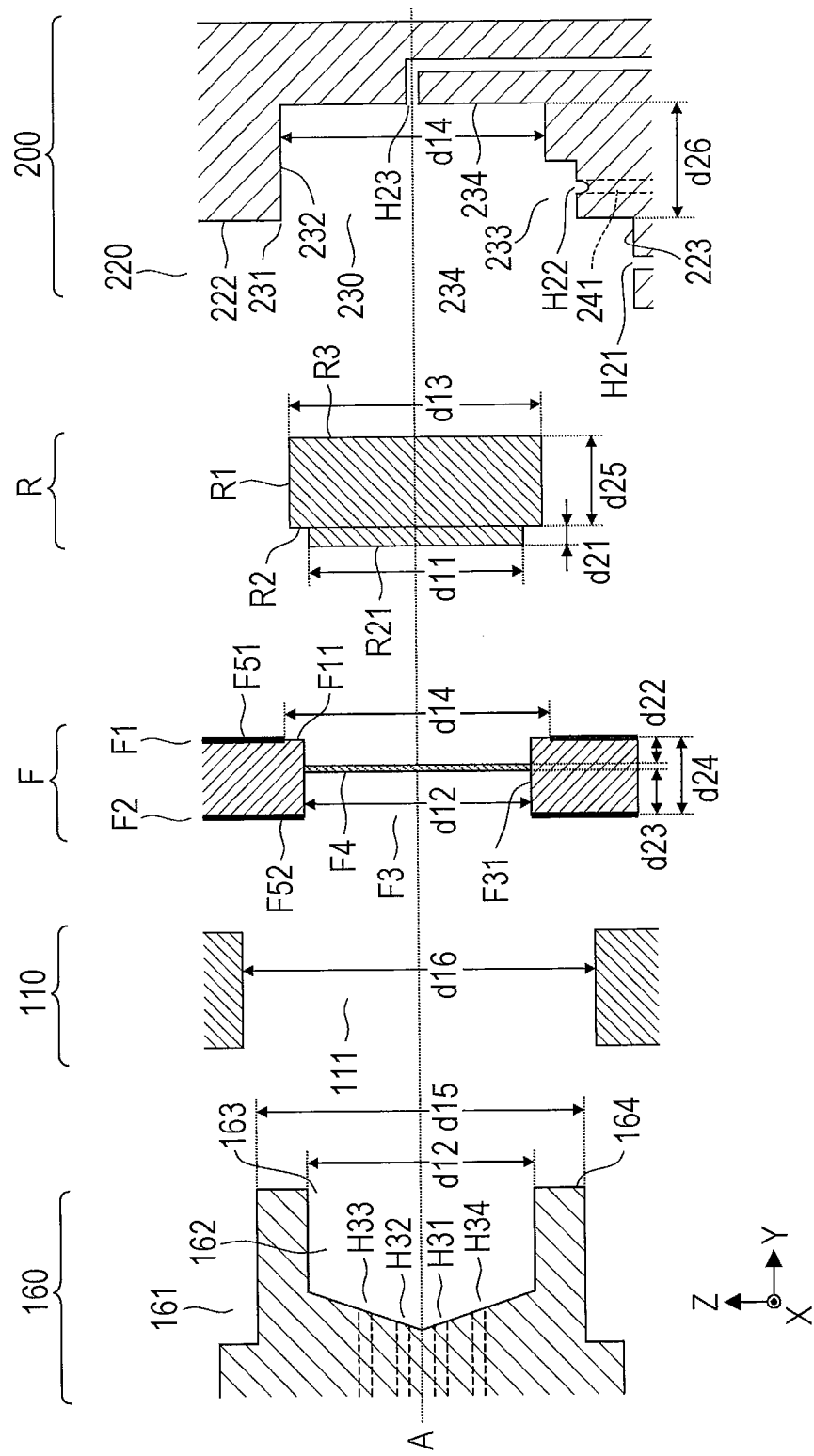
FIG. 9 is a cross-sectional view of when the piston, the supporting plate, the filter member, the stirrer, and the accommodating body according to the embodiment are cut along a plane passing through a center axis.

FIG. 9 is a cross-sectional view of when the piston 160, the supporting member 110, the filter member F, the stirrer R, and the accommodating body 200 are cut along the YZ plane passing through the center axis A. In FIG. 9, each section is illustrated in a state spaced apart in the Y-axis direction for the sake of convenience. Furthermore, d11 to d16 indicate the length in the Z-axis direction, and the values of which become large in such order. Moreover, d21 to d26 indicate the length in the Y-axis direction, and the values of which become large in such order.

In the piston 160, the diameter of the recess 162 is d12, and the diameter of the outer circumference of the surface 164 is d15. In the supporting member 110, the diameter of the hole 111 is d16. In the filter member F, the diameter of the hole F3 is d12, the diameter of the outer circumference of the surface F11 is d14, the interval of the surface F1 and the filter F4 is d22, the interval of the surface F2 and the filter F4 is d23, and the interval of the surfaces F1, F2 is d24. In the stirrer R, the diameter of the body portion R1 is d13, the diameter of the projection R21 is d11, the width of the body portion R1 is d25, and the width of the projection R21 including the flange part R21a is d21. In the accommodating body 200, the diameter of the inner side surface 232 is d14, and the width of the recess 230 is d26.

The recess 162, the outer circumference of the surface 164, the hole 111, the hole F3, the outer circumference of the surface F119, the body portion R1, the projection R21, and the recess 230 when seen from the Y-axis direction are circular, and the centers of the circles coincide with the center axis A.

FIGS. 10A to 10D are views showing a procedure in which the filter member F is installed in the accommodating unit 220. FIGS. 10A to 10D are cross-sectional views similar to FIG. 9.

FIG. 10A is a view showing a state in which the filter member F is not installed in the accommodating unit 220. In this case, the piston 160 is positioned at the leftmost side, and the surface R3 of the stirrer R is pulled toward the right direction by the magnet 142 (see FIG. 5A) and grounded to the wall portion 234. When the filter member F is inserted into the accommodating unit 220 through the hole 120b of the upper plate 120 and the insertion port 221 of the accommodating unit 220 from the state of FIG. 10A, the state shown in FIG. 10B is obtained. In this case, the filter member F is supported in the upward direction by the bottom surface 223 of the accommodating unit 220.

When the piston 160 is positioned on the rightmost side from the state shown in FIG. 10B, the surface 164 of the piston 160 is pushed against the rubber F52 of the filter member F, and the rubber F51 of the filter member F is pushed against the wall portion 222 of the accommodating unit 220, as shown in FIG. 10C. Thus, the recess 230 and the recess 162 are joined by way of the filter F4. In this case, the opening 231 of the recess 230 is blocked by the filter member F, so that a space S1 closed with respect to the exterior is formed. Furthermore, the opening 163 of the recess 162 is closed by the filter member F, so that a space S2 closed with respect to the exterior is formed.

The space S1 is specifically formed by the side surface on the recess 230 side of the filter F4, the inner side surface F31, the surface F11, the rubber F51, the inner side surface 232, the retaining portion 233, and the wall portion 234. In this case, the space S1 is structurally connected to the exterior through the holes H22, H23. However, the hole H22 is in a substantially closed state since the specimen is retained at the deepest portion of the accommodating unit 210 positioned at the lower end of the flow path 241 beyond the hole H22 during the process of discrimination/substitution. A valve V24 (see FIG. 11) capable of closing the flow path is installed in the flow path beyond the hole H23, and only the diluted solution is externally flowed into the space S1 in the hole H23, so that the hole H23 is in a substantially closed state. Thus, the space S1 is a space closed with respect to the exterior.

As described above, the filter F4 has a hole having a diameter that allows cells, and the like having a smaller diameter than the analyzing target cell to pass through and that does not allow the analyzing target cell to pass through.

The cells, and the like having a smaller diameter than the analyzing target cell in the space S1 thus pass through the filter F4, but the analyzing target cell in the space S1 remains in the space S1.

The space S2 is specifically formed by the side surface on the side opposite to the recess 230 of the filter F4, the inner side surface F31, the rubber F52, and the recess 162. In this case, the space S2 is structurally connected to the exterior through the holes H31 to H34. However, the holes H31 to H34 are in a substantially closed state since a valve capable of closing the flow path is installed in the flow path beyond the holes H31 to H34. Thus, the space S2 is a space closed with respect to the exterior.

When the magnet 142 (See FIG. 5A) is rotated in the state shown in FIG. 10C, the stirrer R is rotated along the side surface (filtering surface) on the recess 230 side of the filter F4 around the center axis A as the center. In this case, the groove R31 is formed in the plane R3 of the stirrer R, as shown in FIG. 7D. Thus, the diluted solution can smoothly flow from the hole H23 into the space S1.

Furthermore, when rotated by the magnet 142, the stirrer R can separate away from the wall portion 234 and move toward the filter member F, as shown in FIG. 10D. However, as shown in FIG. 9, the width d21 of the projection R21 including the flange part R21a is smaller than the interval d22 of the surface F11 and the filter F4, the diameter d11 of the projection R21 is smaller than the diameter d12 of the hole F3, and the outer circumference of the surface R2 (diameter of the body portion R1) d13 is greater than the diameter d14 of the hole F3. As shown in FIG. 10D, the projection R21 including the flange part R21a makes contact with the filter F4 when the surface R2 makes contact with the surface F11 thus preventing the filter F4 from being damaged.

Figure 11:
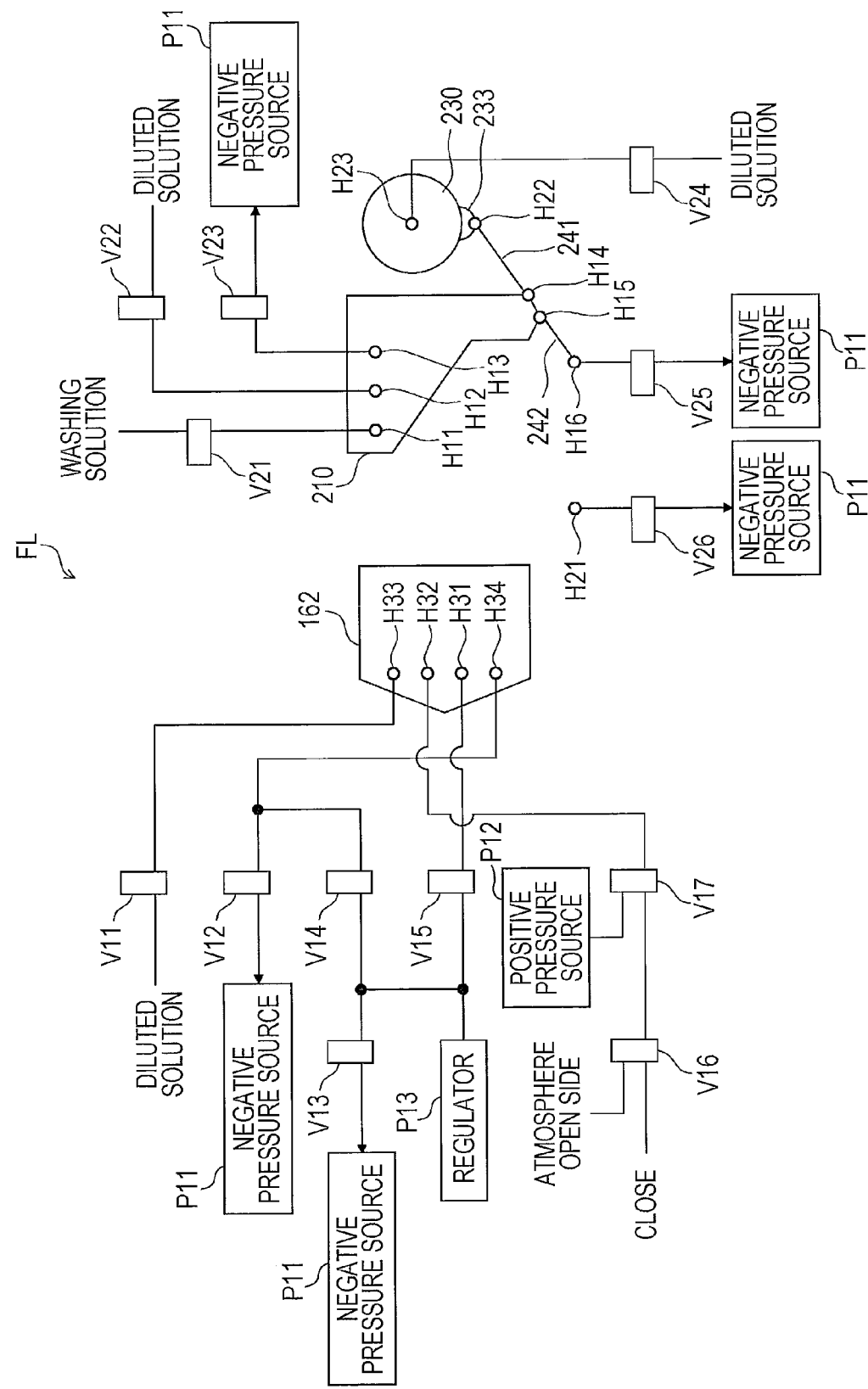
FIG. 11 is a view showing a fluid processing section of a measuring device according to the embodiment.

FIG. 11 is a view showing the fluid processing section FL of the measuring device 2.

The valves V11 to V15, V21 to V26 are configured to be able to switch a state of opening the flow path and a state of closing the flow path. The valves V16, V17 are configured to be able to connect either one of the flow paths connected to the left side with respect to the one flow path on the right side. The holes H31 to H34 are connected to the valve V15, the valve V17, the valve V11, and the valves V12, V14. The holes H11 to H13 are connected to the valves V21 to V23. The holes H23, H16, H21 are connected to the valves V24, V25, V26. A negative pressure source P11 is connected to the valves V12, V13, V23, V25, V26, and a positive pressure source P12 is connected to the valve V17. A regulator P13 for making the pressure constant is connected to the valves V 13 to V15.

FIGS. 12A to 12I are views schematically showing the state of the liquid in the accommodating unit 210 and the spaces S1, S2 in the discriminating/substituting process.

When the discriminating/substituting process is started, the piston 160 and the filter member F are in the state shown in FIG. 10C, and the interior of the accommodating unit 210 and the spaces S1, S2 is washed. The state of the liquid then becomes the state shown in FIG. 12A.

A preparation control section 28 starts the rotation of the stirrer R with the valves V11 to V15 and V21 to V26 closed, the flow path on the atmosphere open side of the valve V 16 closed, and the flow path on the positive pressure source P12 side of the valve V17 closed. The preparation control section 28 then fills the space S1 with the diluted solution. Specifically, the valve V24 is first opened and the diluted solution is supplied into the space S1 through the hole H23. The diluted solution then moves to the accommodating unit 210 through the flow path 241. When a predetermined time has elapsed after the liquid level has reached the height of the pin 212, the valve V24 is closed and the supply of the diluted solution is stopped. The liquid level is in the state shown in FIG. 12B. The valves V13, V15 are then opened, and the negative pressure is applied to the space S2 through the hole H31 by the negative pressure source P11, whereby the diluted solution in the space S1 and the accommodating unit 210 is suctioned toward the space S2 through the filter F4. The valves V13, V15 are closed after the space S2 is filled with the diluted solution. Thus, the space S2 is filled with the diluted solution, as shown in FIG. 12C.

The preparation control section 28 then aspirates the specimen from the specimen accommodating portion 12a of the first dispersion section 12 by a volume determined based on the pre-measurement with the sample pipette section 11. The preparation control section 28 then inserts the pipette 11a into the accommodating unit 210 through the hole 120b and the insertion port 211 from the upper side of the upper plate 120, and discharges the aspirated specimen into the accommodating unit 210. The liquid level is then in the state shown in FIG. 12D.

The preparation control section 28 then applies negative pressure to the space S2, and starts the suction of the liquid (diluted solution and specimen) in the space S1 and the accommodating unit 210. Specifically, as the valves V13, V15 are opened and the negative pressure is applied to the space S2 by the negative pressure source P11, the liquid in the space S1 and the accommodating unit 210 is suctioned toward the space S2 through the filter F4. Subsequently, when the liquid level in the accommodating unit 210 reaches the height of the pin 213, as shown in FIG. 12E, the preparation control section 28 closes the valves V13, V15 and stops the suction by the negative pressure after elapse of a predetermined time. The liquid level is thus in the state shown in FIG. 12F.

The preparation control section 28 then applies a counter pressure (positive pressure) to the space S2, and pushes out the cells clogged in the hole of the filter F4 and the cells attached to the surface of the filter F4 on the space S1 side toward the space S1. Specifically, the cells are pushed out into the space S1 by opening the flow path on the positive pressure source P12 side of the valve V17 and applying positive pressure to the space S2 from the positive pressure source P12. After the pushing out by the counter pressure is finished, the flow path on the positive pressure source P12 side of the valve V17 is closed.

The preparation control section 28 then supplies the diluted solution to the accommodating unit 210. Specifically, the valve V24 is opened and the diluted solution is supplied into the space S1 through the hole H23. In this case, the diluted solution moves toward the accommodating unit 210 through the flow path 241. When a predetermined time has elapsed after the liquid level has reached the height of the pin 212, the valve V24 is closed and the supply of the diluted solution is stopped. The liquid level is thereby in the state shown in FIG. 12D. The processes shown in FIGS. 12D to 12F are repeated for a total of three times. Accordingly, the preservative solution having methanol contained in the specimen as the main component is substituted with the diluted solution, and the cells and foreign substances other than the analyzing target cells contained in the specimen are discriminated and transferred toward the space S2. The concentrated solution in which the analyzing target cells are concentrated is generated in the space S1.

The preparation control section 28 then opens the space S2 to atmosphere. Specifically, the flow path on the atmosphere open side of the valve V17 and the valve V16 are opened and the interior of the space S2 is made to atmospheric pressure from when the liquid level is in the state shown in FIG. 12F, so that the liquid in the space S1 moves toward the accommodating unit 210. Subsequently, when the liquid level in the accommodating unit 210 reaches the height of the pin 213, the preparation control section 28 closes the flow path on the atmosphere open side of the valve V17 and the valve V16, stops the opening of the space S2 to atmosphere, and stops the rotation of the stirrer R. The concentrated solution of the analyzing target cell generated in the space S1 is thereby moved from the space 51 toward the accommodating unit 210, so that the liquid level is in the state shown in FIG. 12G. The concentrated solution of the analyzing target cell is thus retained on the lower side of the accommodating unit 210. In this case, the concentration of the concentrated solution is the highest at the lower side of the accommodating unit 210, and becomes lower toward the space S1 from the lower side of the accommodating unit 210.

The preparation control section 28 then inserts the pipette 11a to the deepest portion of the accommodating unit 210 through the hole 120b and the insertion port 211 from the upper side of the upper plate 120, as shown in FIG. 12H. The preparation control section 28 aspirates the concentrated solution retained at the deepest portion of the accommodating unit 210 through the pipette 11a. The liquid level is thus in the state shown in FIG. 12I. The discriminating/substituting process is thereby terminated, and the subsequent processes are carried out based on the concentrated solution aspirated by the pipette 11a.

Figure 13:
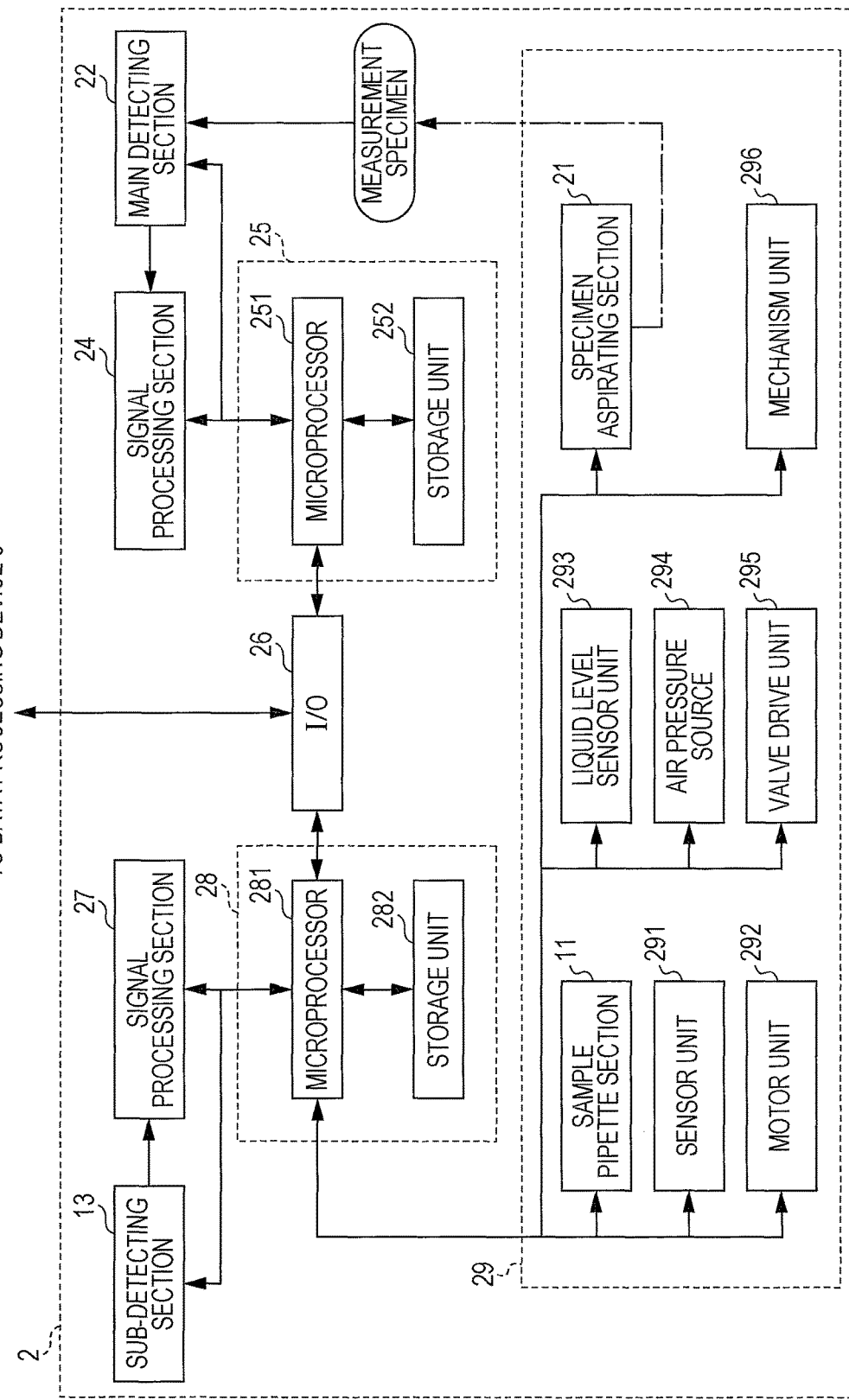
FIG. 13 is a view showing a configuration of a measuring device according to the embodiment.

FIG. 13 is a view showing a configuration of the measuring device 2.

The measuring device 2 includes the sub-detecting section 13 and the main detecting section 22 shown in FIG. 2, and a preparation device section 29 including each section for automatically performing the preparation with respect to the specimen described above. The measuring device 2 also includes the signal processing section 24, a measurement control section 25, an I/O interface 26, the signal processing section 27, and the preparation control section 28.

The sub-detecting section 13 outputs the forward scattered light signal (FSC) by performing the pre-measurement. The signal processing section 27 processes the FSC output from the sub-detecting section 13, and outputs to the preparation control section 28. The preparation control section 28 includes a microprocessor 281 and a storage unit 282. The microprocessor 281 is connected to the preparation device section 29, and is connected to the data processing device 3 and the measurement control section 25 by way of the I/O interface 26.

The preparation device section 29 includes a sensor unit 291, a motor unit 292, the liquid level sensor unit 293, an air pressure source 294, a valve drive unit 295, and the sample pipette section 11 and the specimen aspirating section 21 shown in FIG. 2. A mechanism unit 296 includes other mechanisms shown in FIG. 2. Each unit of the preparation drive section 29 is controlled by the preparation control section 28, and the signal output from each unit of the preparation device section 29 is output to the preparation control section 28.

The sensor unit 291 includes sensors 121, 122, 171, 172 shown in FIG. 4. The motor unit 292 includes a motor 141 shown in FIG. 5A, and a stepping motor connected to the pulley 182 shown in FIG. 5B. The liquid level sensor unit 293 is connected to the pins 212 to 214 shown in FIG. 6C.

The air pressure source 294 includes the negative pressure source P11, the positive pressure source P12, and a positive pressure source for flowing liquid (diluted solution, washing solution, etc.) in the fluid processing section FL. The valve drive unit 295 includes a mechanism for electromagnetically driving each valve and the regulator P13 in the fluid processing section FL shown in FIG. 11.

The main detecting section 22 performs the actual measurement to output the forward scattered light signal (FSC), the side scattered light signal (SSC), and the fluorescence signal (FL). The signal processing section 24 processes the FSC, the SSC, and the FL output from the main detecting section 22, and then outputs to the measurement control section 25. The measurement control section 25 includes a microprocessor 251 and a storage unit 252. The microprocessor 251 is connected to the data processing device 3 and the preparation control section 28 by way of the I/O interface 26.

Figure 14:
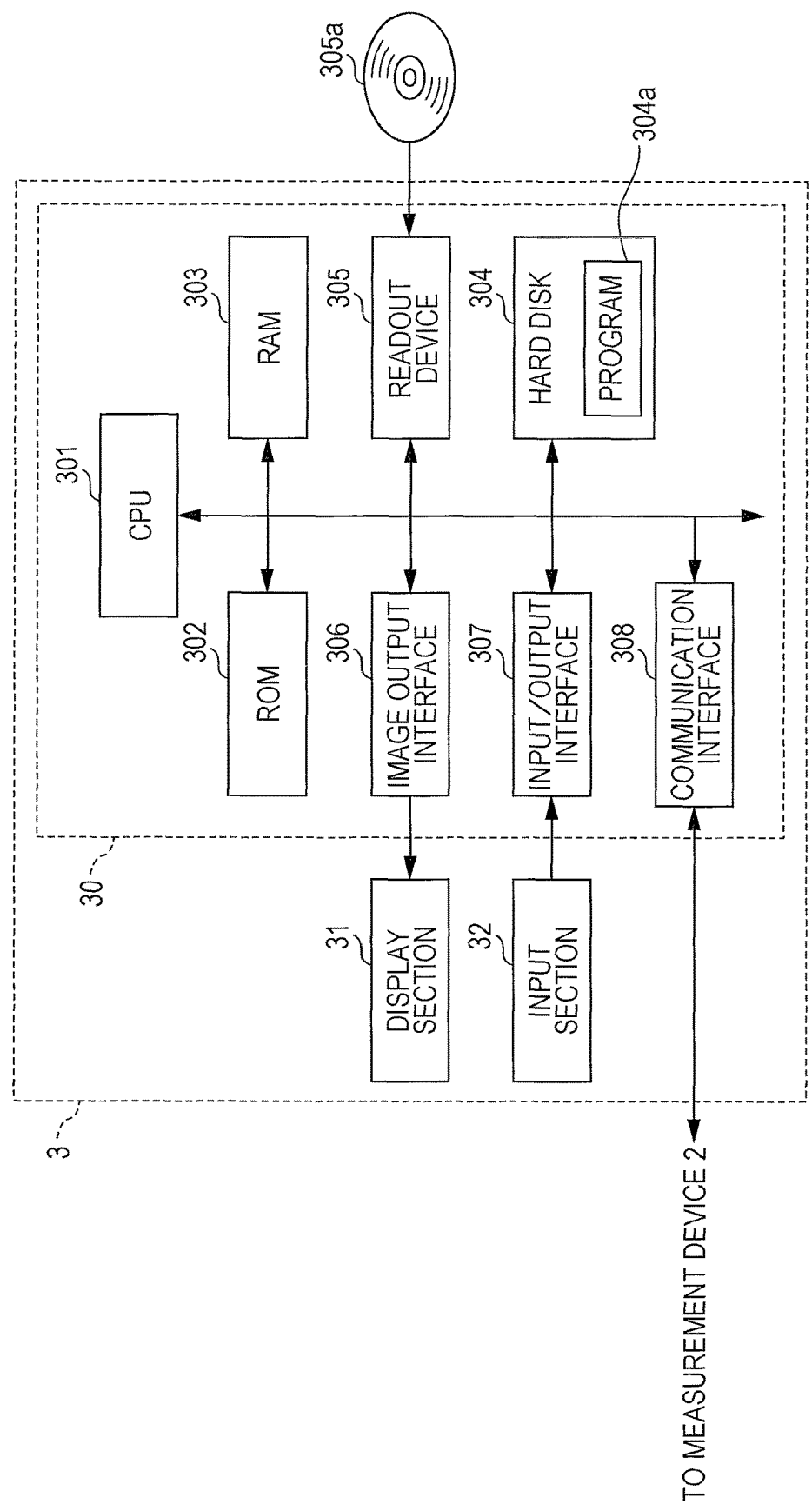
FIG. 14 is a view showing a configuration of a data processing device according to the embodiment.

FIG. 14 is a view showing a configuration of the data processing device 3.

The data processing device 3 includes a personal computer, and is configured by a main body 30, the display section 31, and the input section 32. The main body 30 includes a CPU 301, a ROM 302, a RAM 303, a hard disk 304, a readout device 305, an image output interface 306, an input/output interface 307, and a communication interface 308. The CPU 301 executes the computer program stored in the ROM 302 and the computer program loaded in the ROM 303.

The hard disk 304 is stored with an operating system, a computer program to be executed by the CPU 301, and data used in the execution of the computer program. The hard disk 304 is also stored with a program 304a for performing processes (see FIGS. 15 and 16) to be performed by the data processing device 3. The readout device 305 is configured by a CD drive, a DVD drive, or the like, and is able to read out the computer programs and data recorded in a recording medium 305a. If the program 304a is recorded in the recording medium 305a, the program 304a read out from the recording medium 305a by the readout device 305 is stored in the hard disk 304.

The image output interface 306 outputs an image signal corresponding to the image data to the display section 31, and the display section 31 displays the image based on the image signal output from the image output interface 306. The user inputs instructions through the input section 32, and the input/output interface 307 receives signals input through the input section 32. The communication interface 308 is connected to the measuring device 2, and the CPU 301 transmits and receives the instruction signal and the data with the measuring device 2 through the communication interface 308.

In the cell analyzer 1, a mode (hereinafter referred to as "normal measurement mode") of when measuring the clinical measurement specimen including cells collected from the subject, and a mode (hereinafter referred to as "quality control measurement mode") of when measuring the quality control specimen used for determining the state of the measuring device 2 are prepared. The process in the normal measurement mode and the process in the quality control measurement mode will be described in order below.

Figure 15:
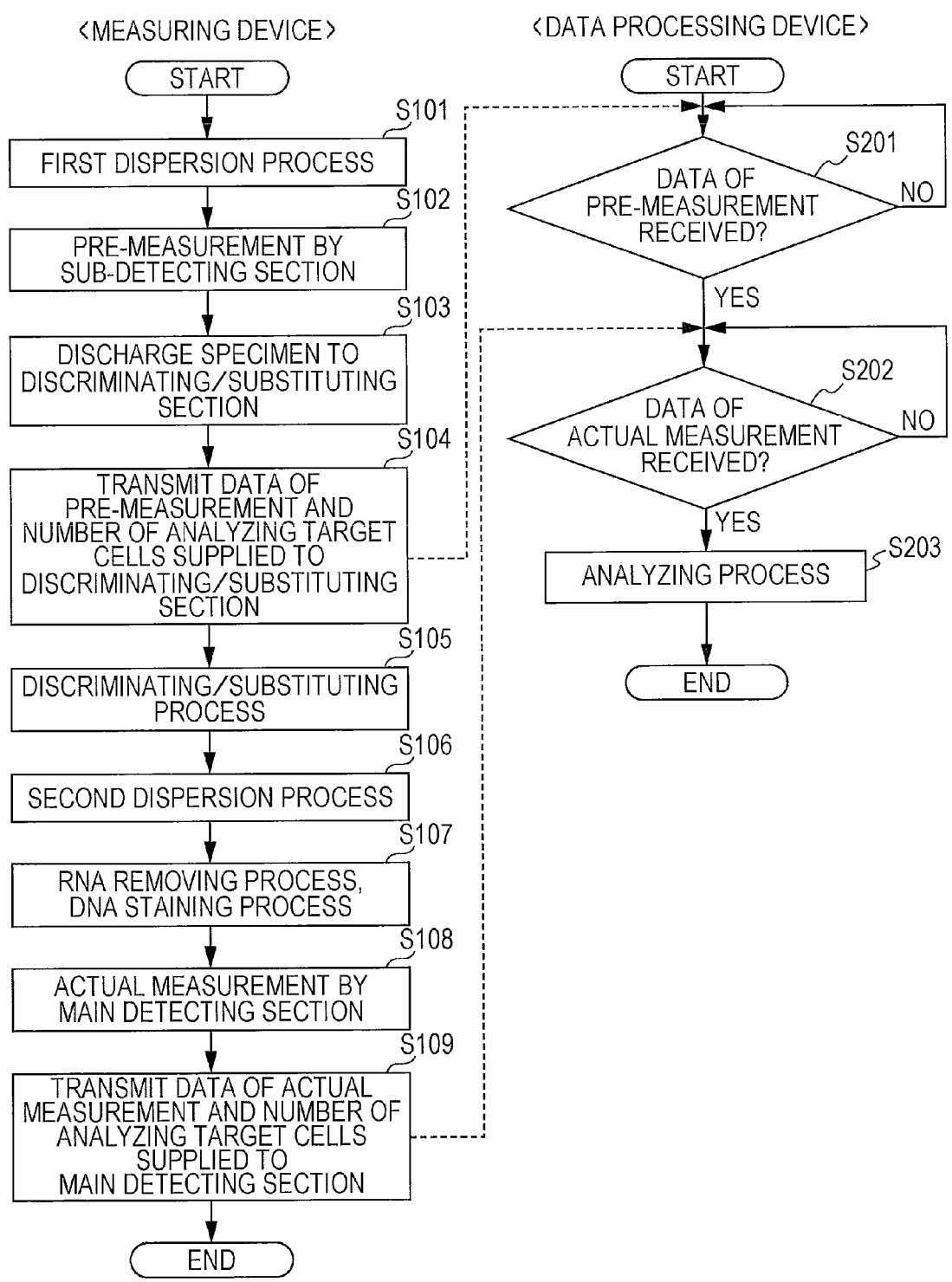
FIG. 15 is a flowchart showing processes of the cell analyzer in a normal measurement mode according to the embodiment.

FIG. 15 is a flowchart showing the process of the cell analyzer 1 in the normal measurement mode.

In the normal measurement mode, the specimen container 4, which contains the mixed solution (specimen) of the preservative solution having methanol as the main component and the cells collected from the subject, is set in the sample setting section 2a (see FIG. 2) by the user, and the process by the cell analyzer 1 is started. When the process is started, the preparation control section 28 of the measuring device 2 performs the first dispersion process on the aggregating cells in the specimen with the first dispersion section 12 (S101).

The preparation control section 28 performs the pre-measurement by the sub-detecting section 13 (S102), and acquires the forward scattered light signal (FSC) for every particle contained in the specimen supplied to the sub-detecting section 13. The preparation control section 28 acquires the number of analyzing target cells supplied to the sub-detecting section 13 based on the width and the peak value of the FSC obtained by the pre-measurement. The preparation control section 28 calculates the concentration of the specimen based on the acquired number of analyzing target cells and the volume of the specimen supplied to the sub-detecting section 13.

The preparation control section 28 then determines the volume of the specimen to be supplied to the discriminating/substituting section 14 based on the calculated concentration and the number of analyzing target cells to be supplied to the discriminating/substituting section 14. Specifically, the volume of the specimen to be supplied to the discriminating/substituting section 14 is determined so that more than necessary analyzing target cells are not supplied to the discriminating/substituting section 14 when the concentration of the specimen is high, and as much analyzing target cells as possible are supplied to the discriminating/substituting section 14 when the concentration of the specimen is low. The preparation control section 28 aspirates the specimen accommodated in the specimen accommodating portion 12a of the first dispersion section 12 by the determined volume, and discharges the aspirated specimen to the accommodating unit 210 of the discriminating/substituting section 14 (S103).

The preparation control section 28 then calculates the number of analyzing target cells supplied to the discriminating/substituting section 14 from the volume of the specimen supplied to the discriminating/substituting section 14 and the concentration of the specimen acquired by the pre-measurement. The preparation control section 28 transmits the data (width and peak value of the FSC of each particle) acquired by the pre-measurement, and the number of analyzing target cells supplied to the discriminating/substituting section 14 to the data processing device 3 (S104). The preparation control section 28 then performs the discrimination/substituting process by the discriminating/substituting section 14 (S105), as described above.

The preparation control section 28 then performs the second dispersion process on the aggregating cells in the specimen with the second dispersion section 16 (S106). The preparation control section 28 then adds the reagent (RNase) to the specimen, performs the RNA removing process of the analyzing target cell in the specimen container 5, adds the reagent (stain solution) to the specimen, and performs the DNA staining process of the analyzing target cell in the specimen container 5 (S107).

The measurement control section 25 of the measuring device 2 performs the actual measurement by the main detecting section 22 (S108), and acquires the forward scattered light signal (FSC), the side scattered light signal (SSC), and the fluorescence signal (FL) for every particle contained in the measurement specimen supplied to the main detecting section 22. The measurement control section 25 acquires the number of analyzing target cells supplied to the main detecting section 22 based on the width and the peak value of the FSC obtained by the actual measurement. The measurement control section 25 transmits the data (width and peak value of the FSC, SSC, FL of each particle) acquired by the actual measurement, and the number of analyzing target cells supplied to the main detecting section 22 to the data processing device 3 (S109).

When the measurement is started, the CPU 301 of the data processing device 3 waits the process until receiving the data, and the like of the pre-measurement transmitted from the measuring device 2 in S104 (S201), and proceeds the process to S202 when receiving the data (S201: YES). The CPU 301 waits the process until receiving the data, and the like of the actual measurement transmitted from the measuring device 2 in S109 (S202), and proceeds the process to S203 when receiving the data (S202: YES). The CPU 301 stores the received data of the pre-measurement, the number of analyzing target cells supplied to the discriminating/substituting section 14, the data of the actual measurement, and the number of analyzing target cells supplied to the main detecting section 22 in the hard disk 304.

The CPU 301 then performs the analyzing process based on the FSC, the SSC, and the FL obtained by the actual measurement (S203). Specifically, the characteristic parameters such as the forward scattered light intensity, the fluorescence intensity, and the like are acquired, and the frequency distribution data for analyzing cells and nuclei are created based on such characteristic parameters. The CPU 301 performs the discriminating process of the particles in the measurement specimen based on the frequency distribution data, and determines whether or not the analyzing target cell is abnormal, specifically, whether or not a cancerous cell (atypical cell). Subsequently, the CPU 301 displays the analysis result on the display section 31. The process of the cell analyzer 1 in the normal measurement mode is thereby terminated.

FIG. 16 is a flowchart showing the process of the cell analyzer 1 in the quality control measurement mode. In the process of the measuring device 2 in this case, S111, S112 are added in place of S104, S109 in the process of the measuring device 2 of the normal measurement mode shown in FIG. 15. Furthermore, in the process of the data processing device 3 in this case, S211 to S214 are added in place of S203 in the process of the data processing device 3 of the normal measurement mode shown in FIG. 15.

In the quality control measurement mode, the two specimen containers 4 containing the mixed solution (specimen) of the preservative solution having methanol as the main component and the quality control specimen are set in the sample setting section 2a (see FIG. 2) by the user, and the process by the cell analyzer 1 is started. The specimens in the two specimen containers 4 used in the quality control measurement mode are taken into the measuring device 2 in order and processed. The quality control specimen contains particles (hereinafter referred to as "quality control particle") having a particle diameter of the same extent as the analyzing target cell, where the diameter of the quality control particle is set to a value greater than the diameter (10 µm) of the hole of at least the filter F4, and is 15 µm in the present embodiment.

When the process is started, the entire amount of specimen in the specimen container 4 is aspirated, and discharged to the specimen accommodating portion 12a of the first dispersion section 12. The preparation control section 28 of the measuring device 2 performs the first dispersion process on the quality control particle in the specimen with the first dispersion section 12 (S101), similar to the normal measurement mode. A part of the specimen completed with the first dispersion process and accommodated in the specimen accommodating portion 12a is discharged to the specimen take-in portion 13a of the sub-detecting section 13. Thus, the specimen having the volume v1 remains in the specimen accommodating portion 12a.

The preparation control section 28 then performs the pre-measurement by the sub-detecting section 13 (S102). The preparation control section 28 acquires the number of quality control particles supplied to the sub-detecting section 13 based on the width and the peak value of the FSC obtained by the pre-measurement. The preparation control section 28 calculates a concentration c1 of the relevant specimen based on the acquired number of quality control particles and the volume of the specimen supplied to the sub-detecting section 13. The preparation control section 28 aspirates all the specimens having the volume v1 accommodated in the specimen accommodating portion 12a of the first dispersion section 12, and discharges the aspirated specimens to the accommodating unit 210 of the discriminating/substituting section 14 (S103).

The preparation control section 28 calculates the number n2 of quality control particles supplied to the discriminating/substituting section 14 by performing the computation of v1×c1 based on the volume v1 of the specimen supplied to the discriminating/substituting section 14 and the concentration c1 of the specimen acquired by the pre-measurement. The preparation control section 28 then transmits the data of each particle, including width and peak value of the FSC, acquired by the pre-measurement and the number n2 of quality control particles supplied to the discriminating/substituting section 14 to the data processing device 3 (S111). As described above, the preparation control section 28 performs the discriminating/substituting process by the discriminating/substituting section 14 (S105). The preparation control section 28 then performs the processes of S106, S107, similar to the normal measurement mode.

Similar to the normal measurement mode, the measurement control section 25 of the measuring device 2 then performs the actual measurement by the main detecting section 22 (S108), and acquires the forward scattered light signal (FSC), the side scattered light signal (SSC), and the fluorescence signal (FL) for every particle contained in the measurement specimen supplied to the main detecting section 22. The measurement control section 25 acquires a number n3 of quality control particles supplied to the main detecting section 22 based on the width and the peak value of the FSC obtained by the actual measurement. The measurement control section 25 transmits the data of each particle, including widths and peak values of FSC, SSC and FL, acquired by the actual measurement, and the number n3 of quality control particles supplied to the main detecting section 22 to the data processing device 3 (S112).

When the measurement is started, the CPU 301 of the data processing device 3 performs the processes of S201, S202, similar to the normal measurement mode. The CPU 301 stores the received data of the pre-measurement, the number n2 of quality control particles supplied to the discriminating/substituting section 14, the data of the actual measurement, and the number n3 of quality control particles supplied to the main detecting section 22 in the hard disk 304.

The CPU 301 displays a result screen D1 on the display section 31 based on the data, and the like received in S201, S202 (S211). The result screen D1 will be described later with reference to FIG. 17A. The CPU 301 then calculates a collection rate by performing the computation of n3/n2 (S212), and determines whether the calculated collection rate is smaller than a predetermined threshold value R (S213). The threshold value R is set to the same extent as the collection rate of when abnormality is not found in the state of the filter member F. If the collection rate is smaller than the threshold value R (S213: YES), the CPU 301 outputs an alarm through the display section 31 to notify the user that the collection rate is low (S214). The process of the cell analyzer 1 in the quality control measurement mode is thereby terminated.

FIG. 17A is a view showing the result screen D1 showing the measurement result in the quality control measurement mode. The result screen D1 includes 30 numerical display regions D11 including rows i11 to i20 and columns j1 to j3.

The values in the display region D11 of the rows i11 to i15 indicate the width of the forward scattered light signal (FSC) in the pre-measurement, the variation coefficient of the width, the peak value, the variation coefficient of the peak value, and the number of quality control particles. The values in the display region D11 of the rows i16 to i19 indicate the width of the forward scattered light signal (FSC) in the actual measurement, the variation coefficient of the width, the peak value, and the variation coefficient of the peak value. The value in the display region D11 of the row i20 indicates the collection rate acquired in S211 of FIG. 16. The values in the display region D11 of the columns j1, j2 indicate the result with respect to the two specimen containers 4 used in the quality control measurement mode, that is, the results for the first time and the second time. The value in the display region D11 of the column j3 indicates the average of the two results shown in the columns j1, j2.

In the result screen D1 shown in FIG. 17A, determination is made that the measurement result of the second time (column j2) and the average (column j3) of the width (row i11) of the FSC in the pre-measurement are abnormal, and thus the corresponding display region D11 is displayed in red (broken line for the sake of convenience in FIG. 17A). Furthermore, determination is made that the result of the second time (column j2) and the average (column j3) of the collection rate (row i20) are abnormal, and thus the corresponding display region D11 is displayed in red (broken line for the sake of convenience in FIG. 17A). In other words, whether each of the values in the display region D11 of the columns j1 to j3 of the row i20 is smaller than the threshold value R is determined (S213 of FIG. 16), and as a result, the values of the columns j2, j3 of the row i20 are smaller than the threshold value R (S213: YES), and thus the display region D11 of the columns j2, j3 of the row i20 is displayed in red as the output of the alarm of S214.

If the measurement result in the quality control measurement mode includes values determined as abnormal, the corresponding display region D11 is shown in red in the result screen D1 as shown in FIG. 17A and an error list screen D2 shown in FIG. 17B is displayed on the display section 31.

FIG. 17B is a view showing the error list screen D2. The error list screen D2 includes a list D21 and a display region D22.

In the list D21 is displayed items determined to be abnormal in the measurement result in the quality control measurement mode. In the list D21 of FIG. 17B is displayed "quality control abnormality 1" indicating that abnormality is found in the forward scattered light signal (FSC), and "quality control abnormality 2" indicating that abnormality is found in the collection rate as shown in FIG. 17A, where the second item (quality control abnormality 2) is selected. The user can select the item by pushing the item in the list D21.

The content to be handled by the user in relation to the selected item of the list D21 is displayed in the display region D22. In the display region D22 of FIG. 17B is displayed the content to be handled by the user when abnormality is found in the collection rate since the "quality control abnormality 2" is selected in the list D21. In other words, the possibility the problems have arose in the filter F4 is displayed as an output of alarm of S214 in the display region D22 of this case, and the necessity of replacing the filter member F is displayed. Thus, if abnormality is found in the measurement result in the quality control measurement mode, the user carries out the necessary actions e.g., replacement of the filter member F and again performs the measurement in the quality control measurement mode.

According to the present embodiment, the diameter of the quality control particle is set to a value greater than the diameter of the hole of the filter F4, and thus the quality control particles do not move from the space S1 to the space S2 shown in FIG. 10C even if the process by the discriminating/substituting section 14 is carried out if abnormality is not found in the state of the filter member F, similar to the analyzing target cell. Since the quality control particles get lost by attaching to the container, the flow path, and the like before being supplied to the main detecting section 22 after being supplied to the discriminating/substituting section 14, the value of the number n3 of quality control particles supplied to the main detecting section 22 is normally smaller by a certain proportion than the value of the number n2 of quality control particles supplied to the discriminating/substituting section 14. However, if abnormality of the filter member F is found, e.g., the filter member F is not correctly set or the filter F4 is damaged, the quality control particles move from the space S1 to the space S2. Thus, the collection rate calculated by the computation of n3/n2 becomes small compared to when there is no abnormality of the filter member F.

Therefore, if the threshold value R is set to be the same extent as the collection rate of when abnormality is not found in the state of the filter member F, whether abnormality is found in the state of the filter member F can be determined by determining whether the collection rate is smaller than the threshold value R in the quality control measurement mode. If the collection rate is smaller than the threshold value R, the alarm is output as shown in FIGS. 17A and 17B. Thus, the user can recognize that abnormality has occurred in the state of the filter member F.

According to the present embodiment, the pre-measurement is carried out in the sub-detecting section 13 before the specimen is supplied to the discriminating/substituting section 14, and the number n2 of quality control particles supplied to the discriminating/substituting section 14 is acquired based on the measurement data of the specimen by the pre-measurement. Thus, even if the number of quality control particles contained in the specimen container 4 is unknown, the number n2 of quality control particles supplied to the discriminating/substituting section 14 can be acquired. Therefore, whether abnormality has occurred in the state of the filter member F4 can be determined based on the number n2 of quality control particles supplied to the discriminating/substituting section 14 and the number n3 of quality control particles supplied to the main detecting section 22. Furthermore, since the numbers n2, n3 of quality control particles are respectively obtained by the measurement data from the sub-detecting section 13 and the main detecting section 22, the state of the filter member F4 can be rapidly determined compared to when both numbers n2, n3 of quality control particles are obtained by the measurement data from the main detecting section 22, for example.

According to the present embodiment, the filter F4 is arranged in the filter member F, and the filter member F is set in the accommodating unit 220 through the hole 120b shown in FIG. 4 and the insertion port 221 shown in FIG. 6A. Thus, if abnormality is found in the filter member F, the user can rapidly and easily replace the filter member F.

<First Variant>

In the embodiment described above, the number n2 of quality control particles supplied to the discriminating/substituting section 14 is calculated by performing the computation of v1×c1 based on the volume v1 of the specimen supplied to the discriminating/substituting section 14 and the concentration c1 of the specimen acquired by the pre-measurement. In the present variant, the pre-measurement is not carried out in the quality control measurement mode. The number n4 of precision particles contained in the specimen container 4 used in the quality control measurement mode is stored in advance in the hard disk 304 of the data processing device 3. If the number n4 is stored in the recording medium such as the barcode attached to the specimen container 4, the n4 may be read from the recording medium of the specimen container 4 using the reading device such as the barcode reader.

Figure 18:
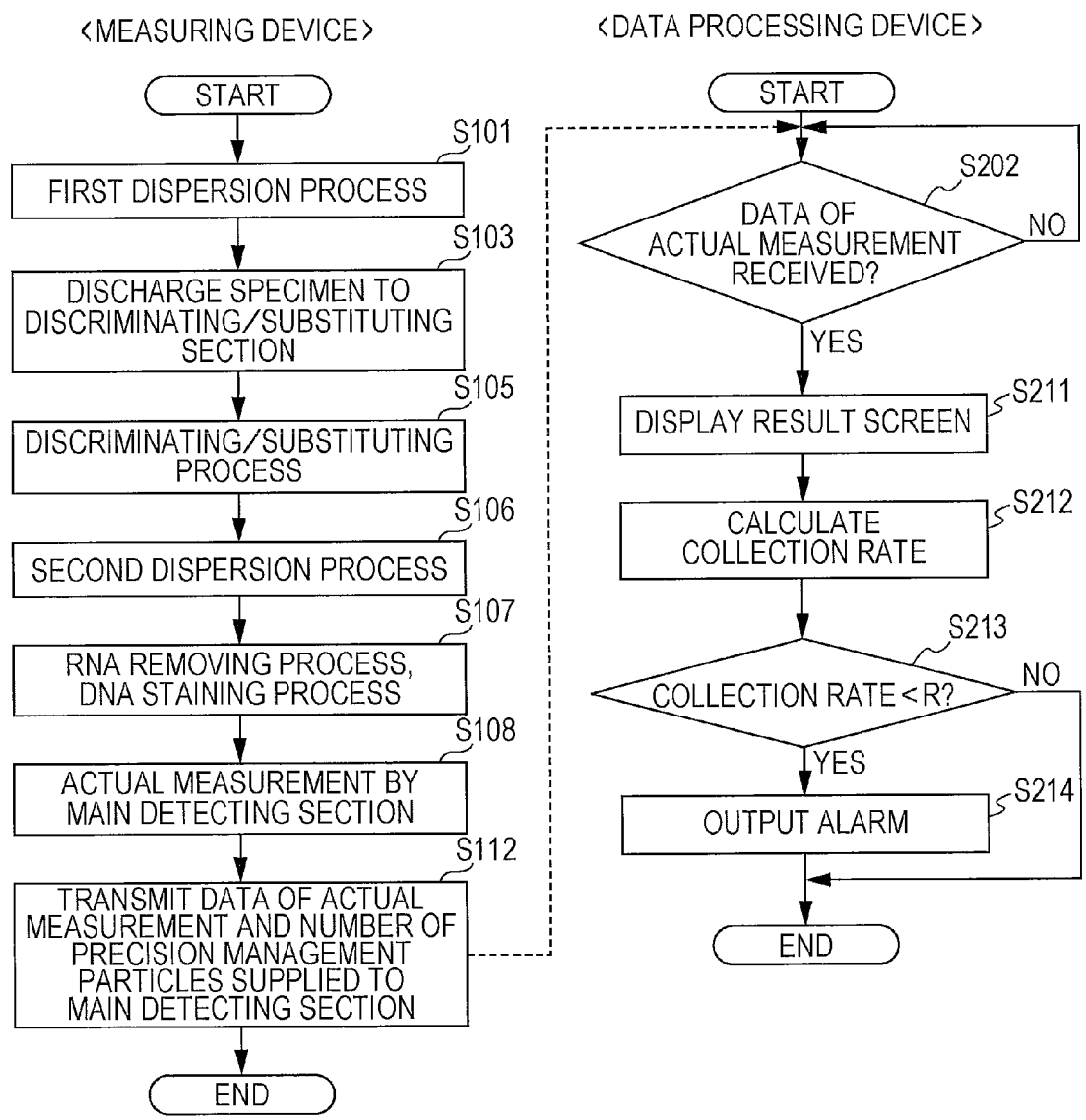
FIG. 18 is a flowchart showing processes of the cell analyzer in the quality control measurement mode according to a first variant.

FIG. 18 is a flowchart showing the process of the cell analyzer 1 in the quality control measurement mode of the present variant. In the process of the measuring device 2 in this case, S102 and S111 are omitted from the process of the measuring device 2 shown in FIG. 16. In the process of the data processing device 3, S201 is omitted from the process of the data processing device 3 shown in FIG. 16.

When the process is started, the entire amount of specimen in the specimen container 4 is aspirated, and discharged to the specimen accommodating portion 12a of the first dispersion section 12. The preparation control section 28 of the measuring device 2 performs the first dispersion process on the quality control particle in the specimen with the first dispersion section 12 (S101), similar to the embodiment described above. The preparation control section 28 then aspirates all the specimens accommodated in the specimen accommodating portion 12a, and discharges the aspirated specimens to the accommodating unit 210 of the discriminating/substituting section 14 (S103). All the quality control particles contained in the specimen container 4 used in the quality control measurement mode are thus discharged to the accommodating unit 210 of the discriminating/substituting section 14, and the number of quality control particles supplied to the discriminating/substituting section 14 becomes n4.

The preparation control section 28 then performs the processes of S105 to S107, similar to the embodiment described above, and the measurement control section 25 performs the processes of S108, S112, similar to the embodiment described above.

When the measurement is started, the CPU 301 of the data processing device 3 performs the process of S202, similar to the embodiment described above. The CPU 301 stores the data of the actual measurement and the number n3 of quality control particles supplied to the main detecting section 22 in the hard disk 304. The CPU 301 then displays the result screen D1 on the display section 31 based on the data, and the like received in S202 (S211). In this case, the number n4 of quality control particles stored in advance in the hard disk 304 is displayed in the display region D11 of the row i15 of the result screen D1.

The CPU 301 performs the computation of n3/n4 based on the number n4 of quality control particles stored in advance in the hard disk 304 and the number n3 of quality control particles supplied to the main detecting section 22 received in S202 to calculate the collection rate (S212). The CPU 301 then performs the processes of S213, S214, similar to the embodiment described above.

According to the present variant, the number n4 of quality control particles contained in the specimen container 4 is stored in advance in the hard disk 304, and thus the pre-measurement does not need to be carried out. The calculation of the collection rate and the output of the alarm are thus rapidly carried out, and hence the user can rapidly recognize if abnormality has occurred in the state of the filter member F.

<Second Variant>

In the embodiment described above, the pre-measurement is carried out in the sub-detecting section 13, but in the present variant, the sub-detecting section 13 is omitted from the measuring device 2 and the pre-measurement is carried out in the main detecting section 22 in the normal measurement mode and the quality control measurement mode. Hereinafter, only the process in the quality control measurement mode will be described.

FIG. 19 is a flowchart showing the process of the cell analyzer 1 in the quality control measurement mode of the present variant. In the process of the measuring device 2 in this case, S121 is added in place of S102 from the process of the measuring device 2 shown in FIG. 16. The process of the data processing device 3 is similar to the process of the data processing device 3 shown in FIG. 16.

When the process is started, the entire amount of specimen in the specimen container 4 is aspirated, and discharged to the specimen accommodating portion 12*a* of the first dispersion section 12. The preparation control section 28 of the measuring device 2 performs the first dispersion process on the quality control particle in the specimen with the first dispersion section 12, similar to the normal measurement mode (S101). A part of the specimen completed with the first dispersion process and accommodated in the specimen accommodating portion 12*a* is supplied to the main detecting section 22, and the pre-measurement is carried out in the main detecting section 22 (S121). The specimen accommodated in the specimen accommodating portion 12*a* is aspirated by the pipette 11*a* and discharged to the specimen container 5, and thereafter, transferred to the main detecting section 22 by the grip portion 15*a* of the container transfer section 15, the holder 18*b* of the rotation table 18*a*, and the pipette 21*a* of the specimen aspirating section 21.

The main detecting section 22 can acquire the forward scattered light signal (FSC), similar to the sub-detecting section 13 of the embodiment described above. The preparation control section 28 calculates the concentration c1 of the specimen based on the number of quality control particles acquired in the pre-measurement by the main detecting section 22 and the volume of the specimen supplied to the main detecting section 22. Similar to the embodiment described above, the preparation control section 28 aspirates all the specimens of volume v1 accommodated in the specimen accommodating portion 12*a* of the first dispersion section 12, and discharges the aspirated specimens to the accommodating unit 210 of the discriminating/substituting section 14 (S103).

The preparation control section 28 then transmits the data (width and peak value of the FSC of each particle) acquired by the pre-measurement and the number n2 (=v1×c1) of quality control particles supplied to the discriminating/substituting section 14 to the data processing device 3 (S111). The preparation control section 28 performs the processes of S105 to S107, similar to the embodiment described above, and the measurement control section 25 performs the processes of S108, S112, similar to the embodiment described above. The processes in the data processing device 3 are also carried out similar to the embodiment described above.

According to the present variant, the pre-measurement is carried out in the main detecting section 22, and hence the configuration of the measuring device 2 can be simplified. In this case as well, the number n2 of quality control particles supplied to the discriminating/substituting section 14 is acquired in the pre-measurement by the main detecting section 22, and thus whether or not abnormality has occurred in the state of the filter member F can be determined based on the collection rate calculated by the computation n3/n2, similar to the embodiment described above.

According to the present variant, the pre-measurement is carried out in the main detecting section 22 before the specimen is supplied to the discriminating/substituting section 14, and the number n2 of quality control particles supplied to the discriminating/substituting section 14 is acquired based on the measurement data of the specimen by the pre-measurement. Thus, similar to the embodiment described above, even if the number of quality control particles contained in the specimen container 4 is unknown, the number n2 of quality control particles supplied to the discriminating/substituting section 14 can be acquired.

<Third Variant>

In the present variant, a flag indicating whether the process of the cell analyzer 1 is possible is stored in the hard disc 304 of the embodiment described above. Such flag is rewritten based on the measurement result obtained in the quality control measurement mode, and the process of the cell analyzer 1 is prohibited or permitted by the value of the flag.

Figure 20A:
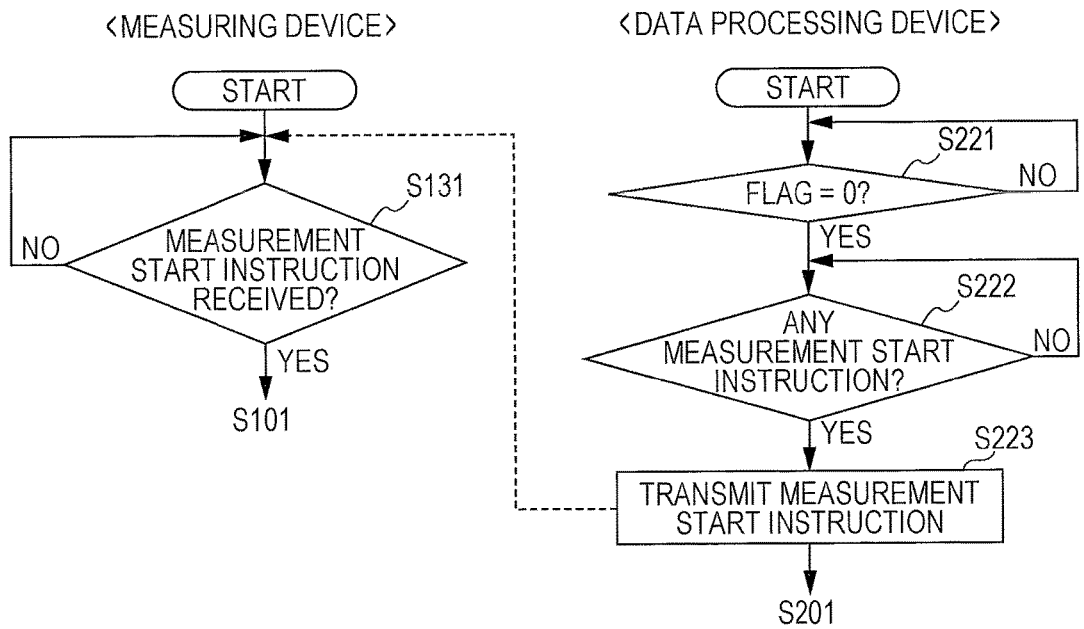
FIG. 20A is a view showing a flowchart showing processes of the cell analyzer in the normal measurement mode according to a third variant.

FIG. 20A is a flowchart showing the process of the cell analyzer 1 in the normal measurement mode of the present variant. In the process of the measuring device 2 in this case, S131 is added to the pre-stage of S101 from the process of the measuring device 2 shown in FIG. 15, and in the process of the data processing device 3, S221 to S223 are added to the pre-stage of S201 from the process of the data processing device 3 shown in FIG. 15. The value of the flag is zero at the start.

When the process is started, the CPU 301 of the data processing device 3 determines whether or not the value of the flag stored in the hard disk 304 is zero (S221). If the value of the flag is zero (S221: YES), the CPU 301 determines whether or not the user made the measurement start instruction through the input section 32 (S222). As shown in FIG. 20C, the user pushes a measurement start button 311 displayed in the display section 31 to input the measurement start instruction. If the measurement start instruction is made (S222: YES), the CPU 301 transmits the measurement start instruction to the measuring device 2 (S223).

When the process is started, the preparation control section 28 of the measuring device 2 determines whether or not the measurement start instruction is received from the data processing device 3 (S131). If the measurement start instruction is received (S131: YES), the preparation control section 28 performs the processes after S101.

Figure 20B:
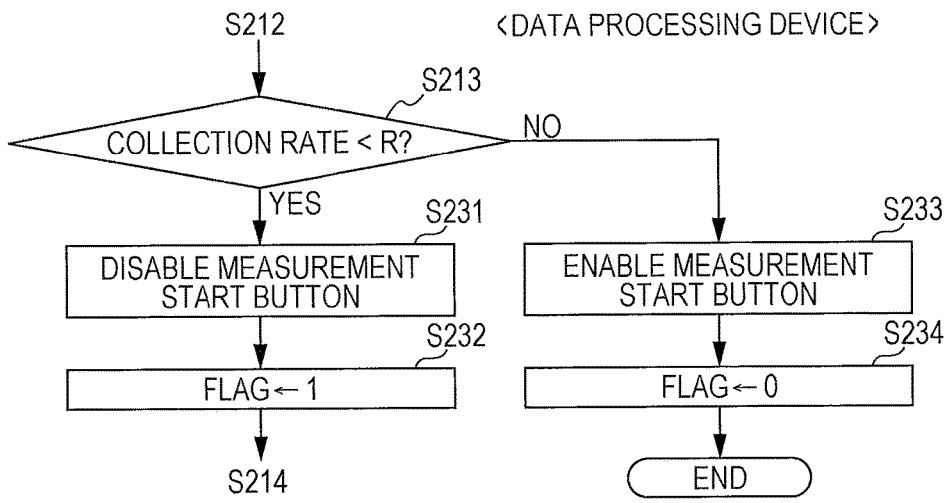
FIG. 20B is a view showing a flowchart showing processes of the cell analyzer in the quality control measurement mode according to the third variant.
Figure 20C:
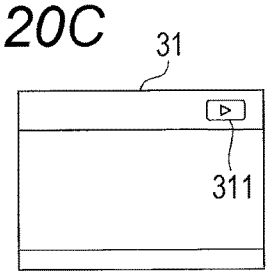
FIG. 20C is a view showing a measurement start button according to the third variant.

FIG. 20B is a flowchart showing the process of the cell analyzer 1 in the quality control measurement mode of the present variant. The process of the measuring device 2 in this case is similar to the process of the measuring device 2 shown in FIG. 16, and in the process of the data processing device 3, S231, S232 are added to the post-stage of when determined as YES in S213, and S233, S234 are added to the post-stage of when determined as NO in S213 from the process of the data processing device 3 shown in FIG. 16.

The CPU 301 of the data processing device 3 disables (state in which the user cannot push) the measurement start button 311 shown in FIG. 20C (S231) when the collection rate is smaller than the threshold value R (S213: YES), that is, when abnormality is found in the state of the filter member F, and sets the value of the flag to one (S232). When the collection rate is greater than or equal to the threshold value R (S213: NO), that is, when abnormality is not found in the state of the filter member F, the measurement start button 311 shown in FIG. 20C is enabled (state in which the user can push) (S233), and the value of the flag is set to zero (S234).

According to the present variant, the process of the cell analyzer 1 is prohibited immediately after the startup of the cell analyzer 1, or when abnormality is found in the state of the filter member F in the quality control measurement mode. The process of the cell analyzer 1 is permitted when the measurement in the quality control measurement mode is carried out and abnormality is not found in the state of the filter member F. Thus, the user can be prevented from making a wrong inappropriate judgment with reference to the analysis result acquired using the filter F4 in a bad state in the normal measurement mode.

In the third variant described above, when the collection rate is smaller than the threshold value R, the setting of the data processing device 3 may be changed so that the analyzing process (S203) is not carried out in the normal measurement mode instead of disabling the measurement start button 311. In this case, when the collection rate is greater than or equal to the threshold value R, the setting of the data processing device 3 is changed so that the analyzing process is carried out in the normal measurement mode. Thus, similar to the third variant described above, the user can be prevented from making the wrong inappropriate judgment with reference to the analysis result acquired using the filter F4 in a bad state in the normal measurement mode.

In the third variant, when the collection rate is smaller than the threshold value R, the setting of the data processing device 3 may be changed so that a mask is applied on the analysis result in the normal measurement mode thereafter instead of disabling the measurement start button 311. In this case, when the collection rate is greater than or equal to the threshold value R, the setting of the data processing device 3 is changed so that the mask is not applied on the analysis result in the normal measurement mode thereafter. Thus, similar to the third variant described above, the user can be prevented from making the wrong inappropriate judgment with reference to the analysis result acquired using the filter F4 in a bad state in the normal measurement mode.

The embodiment of the present invention has been described, but the present invention is not limited to the embodiment described above, and various changes can be made other than the above on the embodiment of the present invention.

For example, in the embodiment described above, the epidermal cells of the uterine cervix are the analyzing target, but other epidermal cells such as buccal cells, bladder, pharynx, and the like, and furthermore, the epidermal cells of organs may be the analyzing target. Furthermore, urine and blood may be the analyzing target. In other words, the present invention can be applied to an apparatus for discriminating the analyzing target cell from the biological specimen with the filter.

In the embodiment described above, the analyzing target cell is retained in the space S1 by the filter F4, and the cells and foreign substances other than the analyzing target cell contained in the specimen are transferred toward the space S2. The concentrated solution of the analyzing target cell remaining in the space S1 is used in the process of post-stage. However, this is not the sole case, and the filter F4 may be set so that the diameter of the hole becomes greater than the analyzing target cell when the analyzing target cell is a cell (e.g., red blood cells) having a small diameter, so that the foreign substances greater than the analyzing target cell are shielded by the filter F4 and only the analyzing target cell can be passed. In this case, if abnormality has occurred in the state of the filter member F, the foreign substances greater than the analyzing target cell pass through the filter F4, and the specimen supplied to the main detecting section 22 contains foreign substances greater than the analyzing target cell. Therefore, if the foreign substance greater than the analyzing target cell is detected in great amount based on the result of the actual measurement by the main detecting section 22 in the quality control measurement mode, determination can be made that abnormality has occurred in the state of the filter member F.

Furthermore, in the embodiment described above, the alarm is output through the display section 31 as shown in FIGS. 17A and 17B in S214, but this is not the sole case, and an alarm sound may be output from a speaker installed in the data processing device 3. The configuration in which the data processing device 3 outputs the alarm is not the sole case, and the measuring device 2 may output the alarm using the display section, the speaker, and the like.

In the embodiment described above, the number of quality control particles supplied to the discriminating/substituting section 14 is acquired by the pre-measurement by the sub-detecting section 13, and the number of quality control particles supplied to the main detecting section 22 is acquired by the actual measurement by the main detecting section 22. Whether or not abnormality has occurred in the state of the filter member F is determined based on the acquired numbers of quality control particles. However, this is not the sole case, and the turbidity of the quality control specimen may be acquired as a value reflecting the amount of quality control particles in the pre-measurement and the actual measurement, and the state of the filter member F may be determine based on the turbidity of the quality control specimen supplied to the discriminating/substituting section 14 and the turbidity of the quality control specimen supplied to the main detecting section 22.

In the embodiment and the second variant described above, a ratio (collection rate) of the number n3 of quality control particles supplied to the main detecting section 22 and the number n2 of quality control particles supplied to the discriminating/substituting section 14 is calculated, and the alarm is output when the collection rate is smaller than the threshold value R, but the present invention is not limited thereto. For example, the difference between n3 and n2 may be calculated, and the alarm may be output when the difference is greater than a predetermined threshold value.

In the first variant, the ratio (collection rate) of the number n3 of quality control particles supplied to the main detecting section 22 and the number n4 of quality control particles contained in the specimen container 4 used in the quality control measurement mode is calculated, and the alarm is output when the collection rate is smaller than the threshold value R, but the present invention is not limited thereto. For example, the difference between n3 and n4 may be calculated, and the alarm may be output when the difference is greater than a predetermined threshold value.

In the embodiment described above, the flow cytometer 40 of the sub-detecting section 13 is configured to receive only the forward scattered light signal (FSC), but may be configured to further receive the side scattered light signal (SSC) and the fluorescence signal (FL), similar to the flow cytometer 50 of the main detecting section 22. In this case, the number of analyzing target cells is acquired based on the forward scattered light (FSC) in the sub-detecting section 13, but the number of analyzing target cells may be acquired based on the side scattered light signal (SSC) and the fluorescence signal (FL). The number of analyzing target cells is acquired based on the forward scattered light (FSC) in the main detecting section 22, but the number of analyzing target cells may be acquired based on the side scattered light signal (SSC) and the fluorescence signal (FL).

In the embodiment described above, the sub-detecting section 13 and the main detecting section 22 are configured by a flow cytometer, but the detecting sections may be configured by an electrical resistance type detecting section.

In the embodiment described above, the discriminating/substituting section 14 is installed in the measuring device 2, but this is not the sole case, and may be installed in the cell collecting apparatus different from the measuring device 2. The cell collecting apparatus in this case includes the discriminating/substituting section 14, the specimen supplying section configured to supply the specimen to the discriminating/substituting section 14 similar to the sample pipette section 11, the measuring section configured to optically measure the quality control specimen, and the information processing section configured to process the measurement data obtained by the measuring section. In the quality control measurement mode, the cell collecting apparatus performs the process on the quality control specimen with the discriminating/substituting section 14 and measures the quality control specimen after the processing by the discriminating/substituting section 14 with the measuring section. The information processing section determines the state of the filter member F, similar to the above embodiment, based on the measurement data obtained by the measuring section, and outputs an alarm based on the determination result. The cell collecting apparatus performs the process on the biological specimen with the discriminating/substituting section 14 in the normal measurement mode. The biological specimen after the processing by the discriminating/substituting section 14 is appropriately transferred to the measuring device 2, and the measurement of the biological specimen is carried out by the main detecting section 22 of the measuring device 2.

In addition, various changes can be appropriately made on the embodiment of the present invention within a scope of the technical concept described in the Claims.

What is claimed is:
1. A cell analyzer comprising:
    a measuring device that includes:
        a collecting section configured to collect target cells in a clinical specimen collected from a subject and quality control particles in a quality control specimen with a filter, wherein the filter is provided with pores of a size capable of capturing the quality control particles;
        a flow cell having a flow channel that accommodates a flow of the target cells and the quality control particles collected by the collecting section;
        an optical source configured to irradiate the target cells and the quality control particles flowing through the flow cell with light;
        a light detector configured to detect light from each of the target cells and the quality control particles irradiated by the optical source; and
    a data processing device programmed to:
        operate the cell analyzer in a first mode measuring the clinical specimen and
        in a second mode, which:
            conducts first measurement of the quality control particles in the quality control specimen before being collected by the collecting section and
            conducts a second measurement of the quality control particles in the quality control specimen after being collected by the collecting section;
            acquires a first value reflecting an amount of quality control particles based on detection data obtained from the first measurement and a second value reflecting an amount of quality control particles collected by the collecting section based on detection data obtained from the second measurement; and
            outputs an alarm based on the first value and the second value.

2. The cell analyzer according to claim 1, wherein the data processing device is further programmed to obtain a ratio between the first value and the second value, and
    the data processing device is programmed to output the alarm based on a comparison result of comparing the obtained ratio with a ratio threshold value.

3. The cell analyzer according to claim 1, wherein the measuring device further comprises a detecting section configured to detect the quality control particles in the quality control specimen before being collected by the collecting section, and the flow cell flows therethrough the quality control particles in the quality control specimen after being collected by the collecting section.

4. The cell analyzer according to claim 1, wherein the quality control specimen contains a known amount of quality control particles.

5. The cell analyzer according to claim 1, wherein the collecting section is configured to supply the filter with a collecting solution to disperse the target cells or the quality control particles captured by the filter ire the collecting solution; and
    the flow cell accommodate a flow of the collecting solution including the target cell.

6. The cell analyzer according to claim 1, wherein the data processing device is further programmed to output an alarm that ages replacement of the filter.

7. The cell analyzer according to claim 1, wherein the data processing device is further programmed to prohibit analysis of a clinical specimen in the first mode when the first value and the second value meet a predetermined condition.

8. The cell analyzer according to claim 1, wherein the collecting section detachably holds the filter.

9. The cell analyzer according to claim 1, wherein the data processing device is further programmed to analyze epidermal cells of a uterine cervix in the clinical specimen as the target cells in the first mode.

10. The cell analyzer according to claim 1, wherein the data processing device is further programmed to determine whether the target cells are cancer cells based on detection data of the target cells in the first mode.

11. A cell collecting apparatus comprising:
a filter having pores therein;
a specimen supplying section configured to supply a clinical specimen containing target cells and a quality control specimen containing quality control particles to the filter, wherein the filter is provided with pores of a size capable of capturing the quality control particles;
a collecting solution supplying section configured to supply a collecting solution to the filter to collect the target cells and the quality control particles captured by the filter;
a flow cell having a flow channel accommodating a flow of the collecting solution containing the target cells and the quality control particles captured by the filter;
an optical source configured to irradiate the target cells and the quality control particles flowing through the flow cell with light;
a light detector configured to detect light from each of the target cells and the quality control particles irradiated by the optical source; and
a data processing device programmed to:
cause the specimen supplying section to supply the quality control specimen containing the quality control particles;
cause the collecting solution supplying section to collect the quality control particles of the quality control specimen captured by the filter;
cause the optical source to irradiate the collected quality control particles flowing through the flow cell to detect, by the light detector, light from each of the collected quality control particles;
acquire a first value reflecting an amount of the quality control particles in the quality control specimen based on detection data obtained by the light detector before collecting the quality control particles captured by the filter;
acquire a second value reflecting an amount of the collected quality control particles in the quality control specimen based on detection data obtained by the light detector after collecting the quality control particles captured by the filter; and
output an alarm based on the first value and the second value.

12. The cell collecting apparatus according to claim 11, wherein the data processing device is programmed to obtain a ratio of the first value and the second value, and output the alarm based on a comparison result of comparing the ratio with a ratio threshold value.

13. The cell collecting apparatus according to claim 11, further comprising a detecting section configured to detect the quality control particles in the quality control specimen before being collected by the collecting section, and wherein the flow cell flows therethrough the quality control particles in the quality control specimen after being collected by the collecting section.

14. The cell collecting apparatus according to claim 11, wherein the collecting section detachably holds the filter.

15. The cell collecting apparatus according to claim 11, wherein the data processing device is programmed to output an alarm that urges replacement of the filter.

16. A quality control method of a cell analyzer including a filter, a flow cell, an optical source, a light detector and an outputting section, the method comprising:
supplying a quality control specimen containing quality control particles to the filter, wherein the filter is provided with pores of a size capable of capturing the quality control particles;
flowing the quality control particles captured by the filter through the flow cell;
irradiating, by the optical source, the quality control particles flowing through the flow cell with light;
detecting, by the light detector, light from each of the quality control particles irradiated by the optical source;
acquiring a first value reflecting an amount of the quality control particles in the quality control specimen based on detection data obtained by the light detector before supplying the quality control particles to the filter;
acquiring a second value reflecting an amount of the quality control particles captured by the filter based on detection data obtained by the light detector; and
outputting, by the outputting section, an alarm of urging a replacement of the filter based on the first value and the second value.

17. A cell analyzer comprising:
a measuring device that includes:
a collecting section configured to collect target cells in a clinical specimen collected from a subject and quality control particles in a quality control specimen with a filter, wherein the filter is provided with pores of a size capable of capturing quality control particles;
a flow cell having a flow channel that accommodates a flow of the target cells and the quality control particles collected by the collecting section;
an optical source configured to irradiate the target cells and the quality control particles flowing through the flow cell with light;
a light detector configured to detect light from each of the target cells and the quality control particles irradiated by the optical source; and
a data processing device is programmed to:
measure the quality control specimen containing the quality control particles, wherein the quality control measurement includes a first measurement of measuring the quality control particles before being collected by the collecting section and a second measurement of measuring the quality control particles after being collected by the collecting section,
acquire a first value reflecting an amount of the quality control particles based on detection data obtained from the first measurement and a second value reflecting an amount of the quality control particles collected by the collecting section based on detection data obtained from the second measurement, and
output an alarm based on the first value and the second value.

* * * * *

UNITED STATES PATENT AND TRADEMARK OFFICE
CERTIFICATE OF CORRECTION

PATENT NO.        : 10,067,116 B2
APPLICATION NO.   : 14/227742
DATED             : September 4, 2018
INVENTOR(S)       : Ryuichiro Ebi et al.

It is certified that error appears in the above-identified patent and that said Letters Patent is hereby corrected as shown below:

In the Claims

In Column 26, Claim 1, Line 11, between "conducts" and "first", insert -- a --

In Column 26, Claim 5, Line 45, delete "ire" and replace with -- in --

In Column 26, Claim 5, Line 47, delete "accommodate" and replace with -- accommodates --

In Column 26, Claim 5, Line 48, delete "cell" and replace with -- cells --

In Column 26, Claim 6, Line 51, delete "ages" and replace with -- urges --

Signed and Sealed this
Twenty-ninth Day of January, 2019

Andrei Iancu
*Director of the United States Patent and Trademark Office*